(12) United States Patent
Watanabe

(10) Patent No.: US 10,080,547 B2
(45) Date of Patent: Sep. 25, 2018

(54) ULTRASOUND DIAGNOSTIC DEVICE AND CONTROL METHOD FOR THE SAME

(71) Applicant: KONICA MINOLTA, INC., Chiyoda-ku, Tokyo (JP)

(72) Inventor: Yasuhito Watanabe, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 400 days.

(21) Appl. No.: 15/052,132

(22) Filed: Feb. 24, 2016

(65) Prior Publication Data
US 2016/0245905 A1 Aug. 25, 2016

(30) Foreign Application Priority Data
Feb. 25, 2015 (JP) ................. 2015-035710

(51) Int. Cl.
A61B 8/00 (2006.01)
G01S 7/52 (2006.01)
(52) U.S. Cl.
CPC ........ *A61B 8/4483* (2013.01); *G01S 7/52049* (2013.01)
(58) Field of Classification Search
CPC ...... A61B 8/00; A61B 8/4483; G01S 7/52049
See application file for complete search history.

(56) References Cited

U.S. PATENT DOCUMENTS 5,348,013 A 9/1994 Kanda et al.
8,926,512 B2 1/2015 Kakee

2008/0242999 A1 10/2008 Kakee
2009/0292207 A1 11/2009 Karasawa
2015/0196284 A1 7/2015 Yamamoto

FOREIGN PATENT DOCUMENTS

| JP | 3091473 B2 | 9/2000 |
| JP | 2008264531 A | 11/2008 |
| JP | 2009279306 A | 12/2009 |
| JP | 2010119481 A | 6/2010 |

(Continued)

OTHER PUBLICATIONS

Itou, et al., "Ultrasound Diagnostic Device", Corona Publishing Co., Ltd., Aug. 26, 2002, pp. 42-45.

(Continued)

*Primary Examiner* — Joseph M Santos Rodriguez
(74) *Attorney, Agent, or Firm* — Holtz, Holtz & Volek PC

(57) ABSTRACT

An ultrasound diagnostic device to which an ultrasound probe having a plurality of transducer elements is connectable. The ultrasound diagnostic device includes ultrasound signal processing circuitry operating as: a delay-and-sum processor; a determiner; and a velocity value calculator. The determiner determines whether adjustment of a velocity value for a partial area in a subject is necessary, based on acoustic line signal intensities for a specific measurement point in the partial area and other measurement points in the partial area. The specific measurement point is selected from among measurement points in the partial area based on acoustic line signals for the measurement points in the partial area. The velocity value calculator, when the determiner determines that velocity value adjustment is necessary, calculates an adjusted velocity value for the partial area by using the acoustic line signal for the specific measurement point.

18 Claims, 26 Drawing Sheets

(56) References Cited

FOREIGN PATENT DOCUMENTS

| JP | 4817728 B2 | 11/2011 |
|---|---|---|
| JP | 2012157387 A | 8/2012 |
| JP | 2014064856 A | 4/2014 |
| JP | 2014068806 A | 4/2014 |
| JP | 5536984 B2 | 7/2014 |

OTHER PUBLICATIONS

Japanese Office Action (and English language translation thereof) dated Apr. 24, 2018 issued in counterpart Japanese Application No. 2015-035710.

FIG. 17

| Imaging area Ci | Coordinates (x, y) | Maximum acoustic line signal intensity Max-i | Velocity value yielding maximum acoustic line signal intensity Max-i |
|---|---|---|---|
| 1 | 79, 248 | 3526 | 1560 [m/s] (Abnormal value) |
| 2 | 63, 536 | 14412 | 1450 [m/s] |
| 3 | 46, 1013 | 5396 | 1470 [m/s] |
| 4 | 94, 1486 | 3383 | 1450 [m/s] |
| 5 | 44, 1898 | 328 | 1400 [m/s] (Abnormal value) |

FIG. 22A

| Imaging area $C_i$ | Coordinates | | Maximum Max-i | Average Avg-i | Adjusted velocity value | Evaluation VI-i | Area whose image quality improves with adjusted velocity value: ◎ Area whose image quality does not improve with adjusted velocity value: ○ |
|---|---|---|---|---|---|---|---|
| | x | y | | | | | |
| 1 | 42 | 212 | 751 | 87 | 1470 | 8.63 | ◎ |
| 2 | 112 | 556 | 4466 | 579 | 1420 | 7.71 | ◎ |
| 3 | 84 | 1155 | 475 | 60 | 1460 | 7.92 | ◎ |
| 4 | 114 | 1393 | 329 | 92 | 1500 | 3.58 | ○ |
| 5 | 8 | 1907 | 76 | 14 | 1440 | 5.43 | ○ |

FIG. 22B

| Imaging area $C_i$ | Coordinates | | Maximum Max-i | Average Avg-i | Adjusted velocity value | Evaluation VI-i | Area whose image quality improves with adjusted velocity value: ◎ Area whose image quality does not improve with adjusted velocity value: ○ |
|---|---|---|---|---|---|---|---|
| | x | y | | | | | |
| 1 | 79 | 248 | 3526 | 617 | 1560 | 5.71 | ◎ |
| 2 | 63 | 536 | 14412 | 1097 | 1450 | 13.13 | ◎ |
| 3 | 46 | 1013 | 5396 | 701 | 1470 | 7.70 | ◎ |
| 4 | 94 | 1486 | 3383 | 457 | 1450 | 7.40 | ◎ |
| 5 | 44 | 1989 | 328 | 96 | 1400 | 3.42 | ○ |

FIG. 22C

| Imaging area $C_i$ | Coordinates | | Maximum Max-i | Average Avg-i | Adjusted velocity value | Evaluation VI-i | Area whose image quality improves with adjusted velocity value: ◎ Area whose image quality does not improve with adjusted velocity value: ○ |
|---|---|---|---|---|---|---|---|
| | x | y | | | | | |
| 1 | 119 | 203 | 10058 | 2121 | 1510 | 4.74 | ○ |
| 2 | 46 | 653 | 16574 | 2530 | 1450 | 6.55 | ◎ |
| 3 | 54 | 1169 | 6741 | 953 | 1420 | 7.07 | ◎ |
| 4 | 48 | 1394 | 4206 | 818 | 1450 | 5.14 | ○ |
| 5 | 10 | 1899 | 540 | 146 | 1460 | 3.70 | ○ |

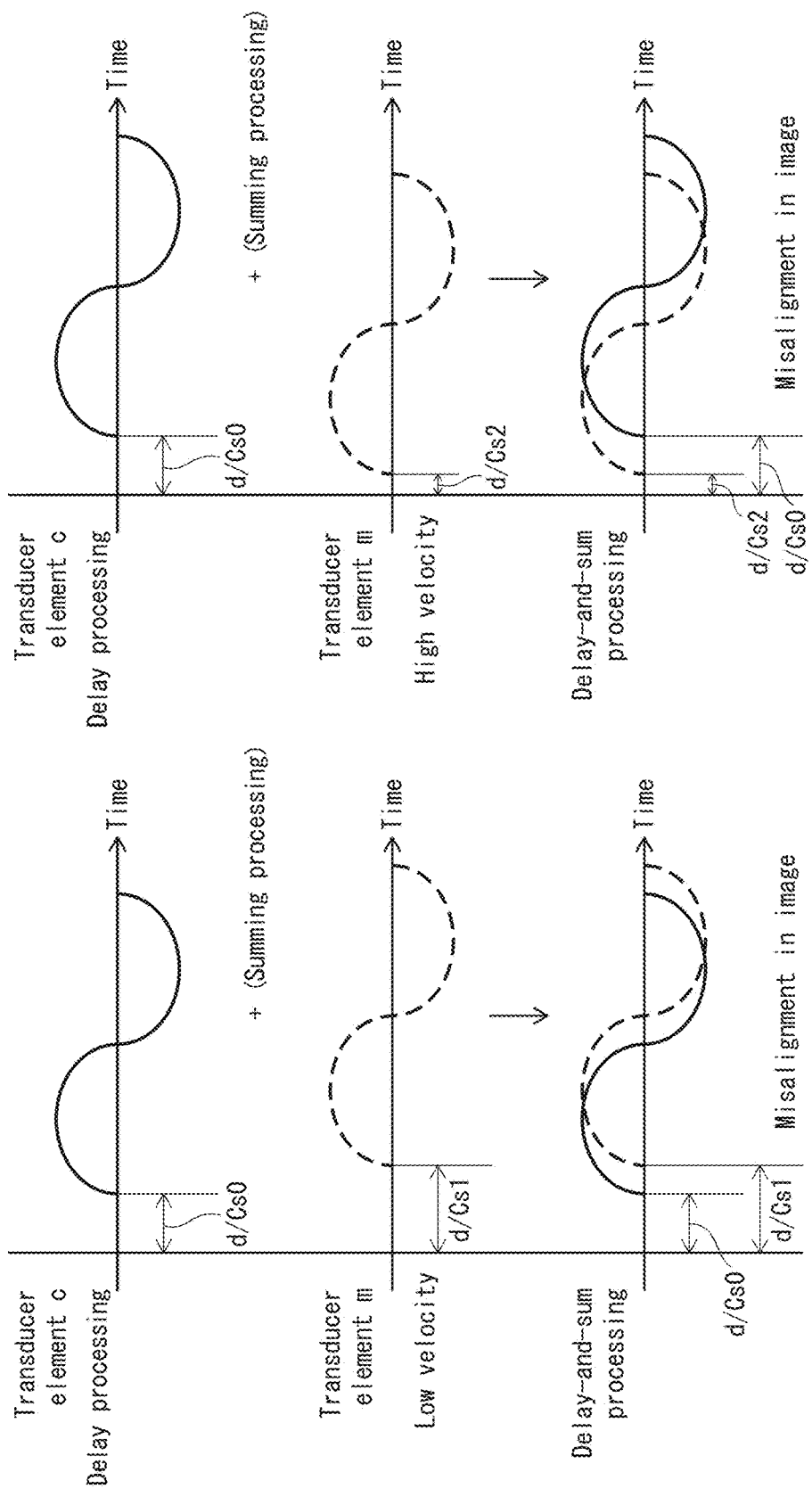

ULTRASOUND DIAGNOSTIC DEVICE AND CONTROL METHOD FOR THE SAME

This application is based on an application No. 2015-35710 filed in Japan, the contents of which are hereby incorporated by reference.

BACKGROUND OF THE INVENTION (1) Field of the Invention

The present disclosure relates to an ultrasound diagnostic device and a control method for the same. In particular, the present disclosure is related to receive beam forming in an ultrasound diagnostic device.

(2) Description of the Related Art

Typically, an ultrasound diagnostic device transmits ultrasound towards the inside of a subject via an ultrasound probe (referred to in the following as a "probe"), and receives reflected ultrasound (an echo) via the probe. The reflected ultrasound is generated within the subject due to tissues in the subject having different acoustic impedances. Further, an ultrasound diagnostic device generates an ultrasound tomographic image based on electric signals acquired through the reception of the reflected ultrasound, and displays the ultrasound tomographic image on a monitor (referred to in the following as a "display unit"). An ultrasound tomographic image shows the structures of tissues inside the subject. Ultrasound diagnostic devices are widely used for the shape diagnosis of subjects, for having low invasiveness and achieving real-time observation of tissues through tomographic images and the like.

A typical method applied in conventional ultrasound diagnostic devices for receive beam forming (i.e., forming signals based on received reflected ultrasound (echo signals)) is so-called delay-and-sum (DAS) beam forming. One example of delay-and-sum beam forming can be found disclosed in pages 42-45 of "Ultrasound Diagnostic Device", written by Masayasu Itou and Tsuyoshi Mochizuki and published by Corona Publishing Co., Ltd (Aug. 26, 2002).

FIG. 24 is a schematic illustrating receive beam forming in a conventional ultrasound diagnostic device. The conventional ultrasound diagnostic device illustrated in FIG. 24 includes a probe 201 and a receive beam former 202. The probe 201 includes a plurality of ultrasound transducer elements (referred to in the following as "transducer elements") 201a that receive ultrasound reflection (echo signals) from the subject. The receive beam former 202 electrically converts the reflected ultrasound received by the transducer elements 201a into analog electronic signals, converts the analog electronic signals into digital electronic signals through some amplification and A/D conversion, and performs delaying and summing of the digital electronic signals. The receive beam former 202 includes an adding unit 2022, and a plurality of delaying units 2021 each associated with a different one of the transducer elements 201a. Specifically, each of the delaying units 2021 performs amplification, A/D conversion, and delaying with respect to an electric signal based on reflected ultrasound obtained by the corresponding transducer element 201a. Further, the adding unit 2022 generates an acoustic line signal by summing electric signals obtained through such processing by the delaying units 2021. The receive beam former 202 outputs the acoustic line signal so generated. Typically, the delay amount that each delaying unit 2021 applies is based on the distance between the corresponding transducer element 201a and a transducer element located along the central axis of the transmitted ultrasound beam. Specifically, suppose that: P denotes a measurement point that corresponds to a given position within the subject and that is located along the central axis of the transmitted ultrasound beam; c denotes a transducer element that is closest to the measurement point P; $d_c$ denotes the distance between the measurement point P and the transducer element c; m denotes a transducer element other than the transducer element c; $d_m$ denotes the distance between the measurement point P and the transducer element m; and Cs0 denotes standard ultrasound velocity within the human body. Here, the time point at which reflected ultrasound from the measurement point P arrives at the transducer element m is later than the time point at which reflected ultrasound from the measurement point P arrives at the transducer element c by a delay amount d/Cs0, which can be calculated by $d_m$/Cs0−$d_c$/Cs0 (refer to FIG. 25A). Thus, by calculating the time point at which reflected ultrasound from the measurement point P arrives at the transducer element c, the time point at which reflected ultrasound from the measurement point P arrives at the transducer element m can be calculated based on the delay amount d/Cs0, which indicates the amount of delay with which reflected ultrasound from the measurement point P arrives at the transducer element m. As such, each delaying unit 2021 specifies a receive signal for the corresponding transducer element 201a by considering the delay with which reflected ultrasound arrives at the corresponding transducer element 201a, and the adding unit 2022 generates an acoustic line signal by summing the receive signals specified by the delaying units 2021 (refer to FIG. 25B).

However, ultrasound velocity in the examination-target part of the subject may differ from the standard ultrasound velocity, depending upon tissue composition. FIGS. 26A and 26B respectively illustrate different velocities Cs1 and Cs2. When ultrasound velocity in the examination target part differs from the standard ultrasound velocity in such a manner, a difference in phase may still be present between receive signals even after delaying is executed with respect to the receive signals, which brings about an image blur in the acoustic line signal acquired through summing the receive signals. In connection with this, Japanese Patent Application Publication No. 2010-119481 discloses one example of technology of setting a plurality of reference areas in an ultrasound scan plane, and determining whether or not the value of ultrasound velocity used in delay-and-sum processing is appropriate based on evaluations of the reference areas.

SUMMARY OF THE INVENTION

Problems to be Solved by the Invention

However, the technology disclosed in Japanese Patent Application Publication No. 2010-119481 requires a great amount of computation for the calculation of evaluations, and further, requires velocity calibration to be conducted prior to actual ultrasound examination. Accordingly, the technology disclosed in Japanese Patent Application Publication No. 2010-119481 requires that velocity calibration be conducted each time the examination-target part of the subject changes, which is inefficient and requires complicated device operation.

In view of such technical problems, the present disclosure provides an ultrasound diagnostic device and a control method for the same that achieve determining the necessity of adjusting a velocity value for delay-and-sum processing through simple computation.

Means for Solving the Problems

One aspect of the present disclosure is an ultrasound diagnostic device to which an ultrasound probe having a plurality of transducer elements is connectable, including: ultrasound signal processing circuitry operating as: a delay-and-sum processor that, for each of a plurality of measurement points respectively corresponding to different positions within a subject, generates an acoustic line signal for the measurement point by summing receive signals for the measurement point, the receive signals respectively corresponding to some or all of the transducer elements and each being generated based on ultrasound reflection that one transducer element receives in response to ultrasound transmission by some or all of the transducer elements towards the subject, wherein for each of the some or all of the transducer elements, the receive signal corresponding to the measurement point is specified taking into account a relative delay in arrival of the ultrasound reflection at the transducer element, the delay being calculated based on a relative distance between the measurement point and the transducer element and a velocity value being an estimated value of ultrasound velocity of a partial area including the measurement point, the partial area corresponding to an area within the subject and being a group of ones of the measurement points for which the same velocity value is applied in the calculation of the delay; a determiner that determines whether or not the velocity value for the partial area is to be adjusted, based on an intensity of an acoustic line signal for a specific measurement point included in the partial area, and intensities of acoustic line signals for at least some of the measurement points included in the partial area, the specific measurement point specified from among the measurement points included in the partial area based on acoustic line signals for at least some of the measurement points included in the partial area; and a velocity value calculator that, when the determiner determines that the velocity value for the partial area is to be adjusted, calculates an adjusted velocity value for the partial area by using the acoustic line signal for the specific measurement point.

BRIEF DESCRIPTION OF THE DRAWINGS

These and the other objects, advantages and features of the technology pertaining to the present disclosure will become apparent from the following description thereof taken in conjunction with the accompanying drawings, which illustrate a specific embodiment of the invention.

In the drawings:

FIG. 17 shows the result of the evaluation of adjusted velocity values conducted in the process for arriving at the ultrasound diagnostic device 100;

Figure 19A:
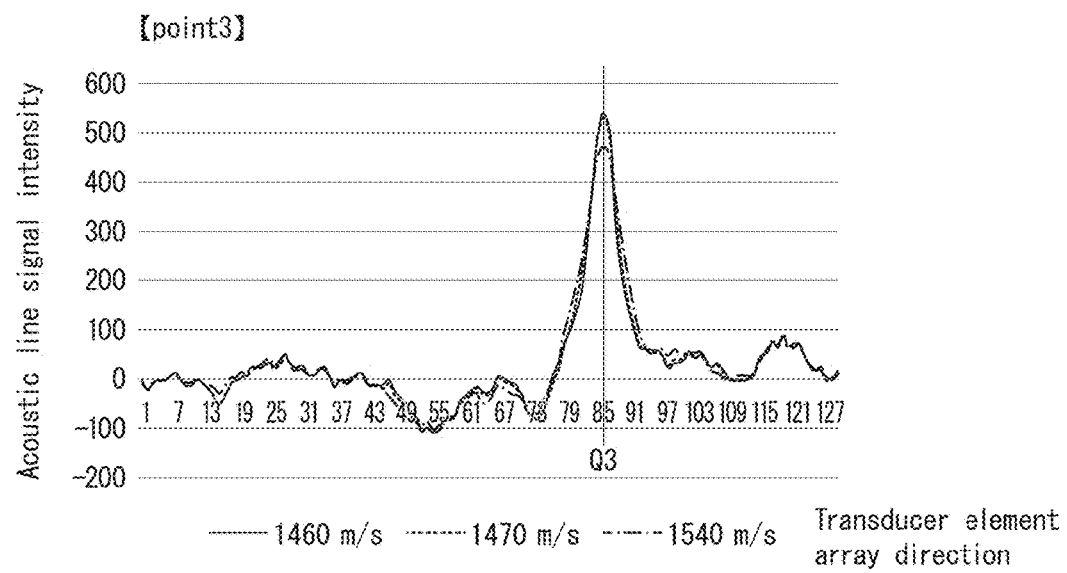
Figure 19B:
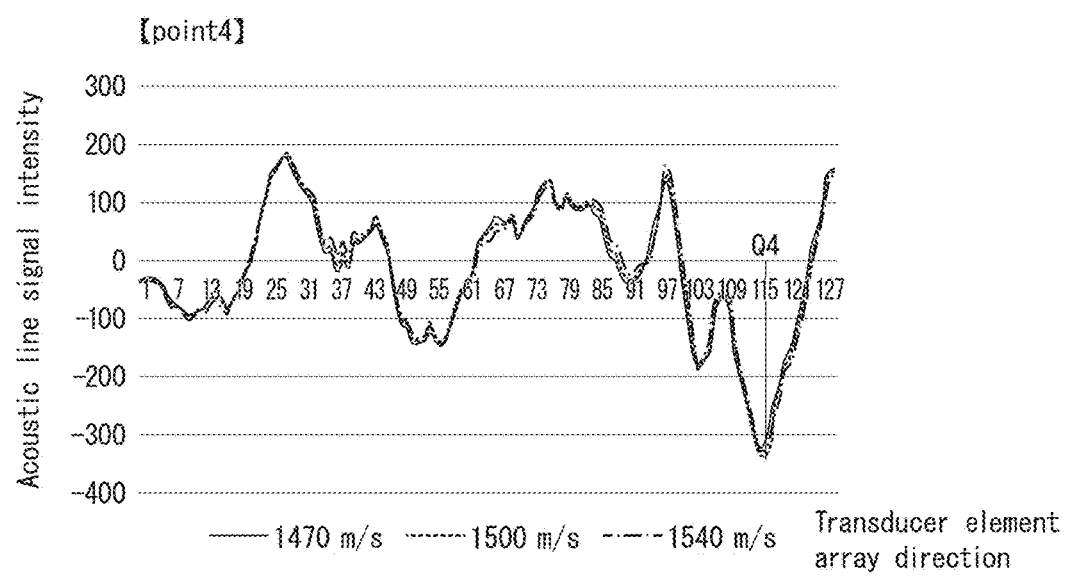
Figure 20:
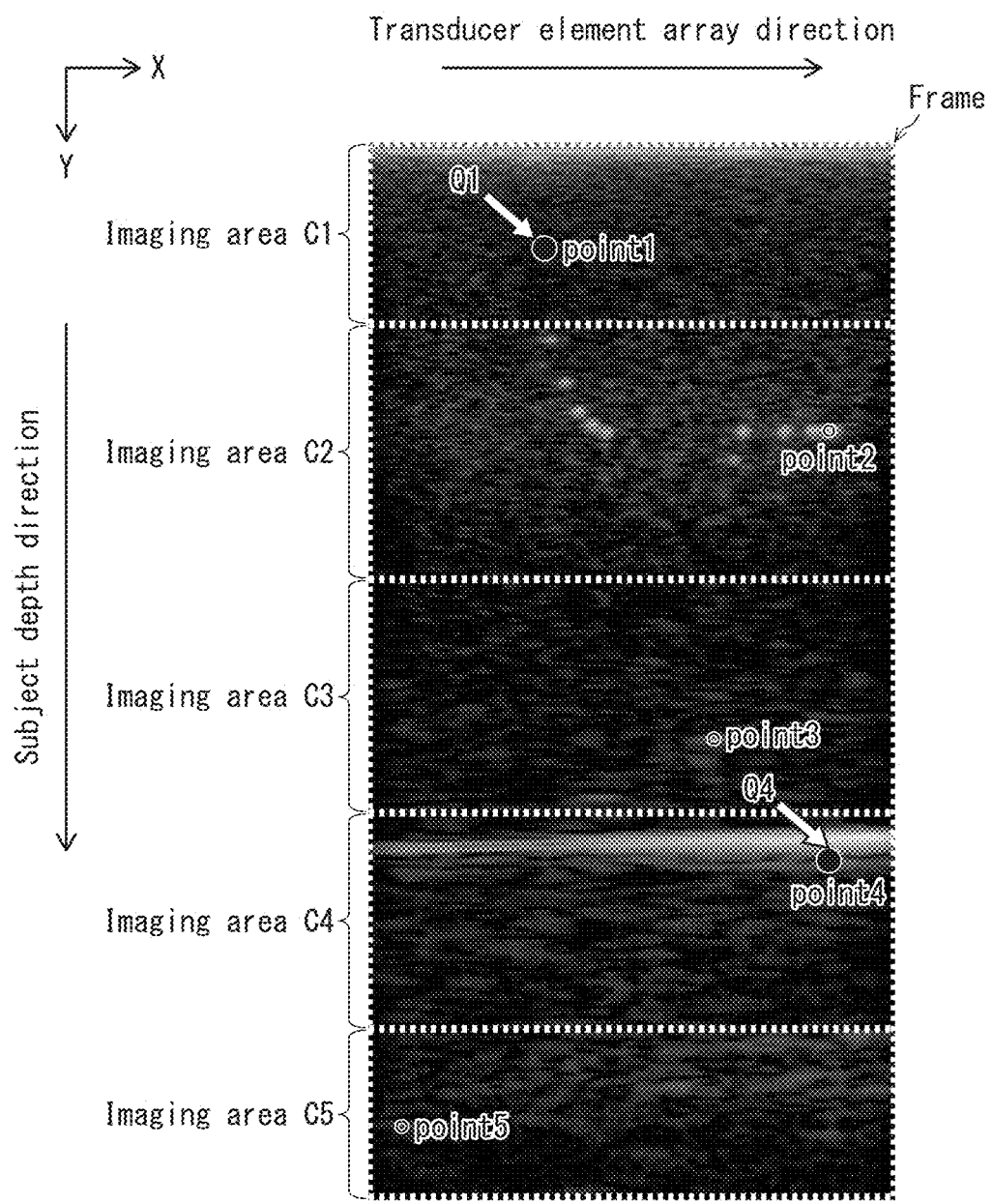
Figure 21:
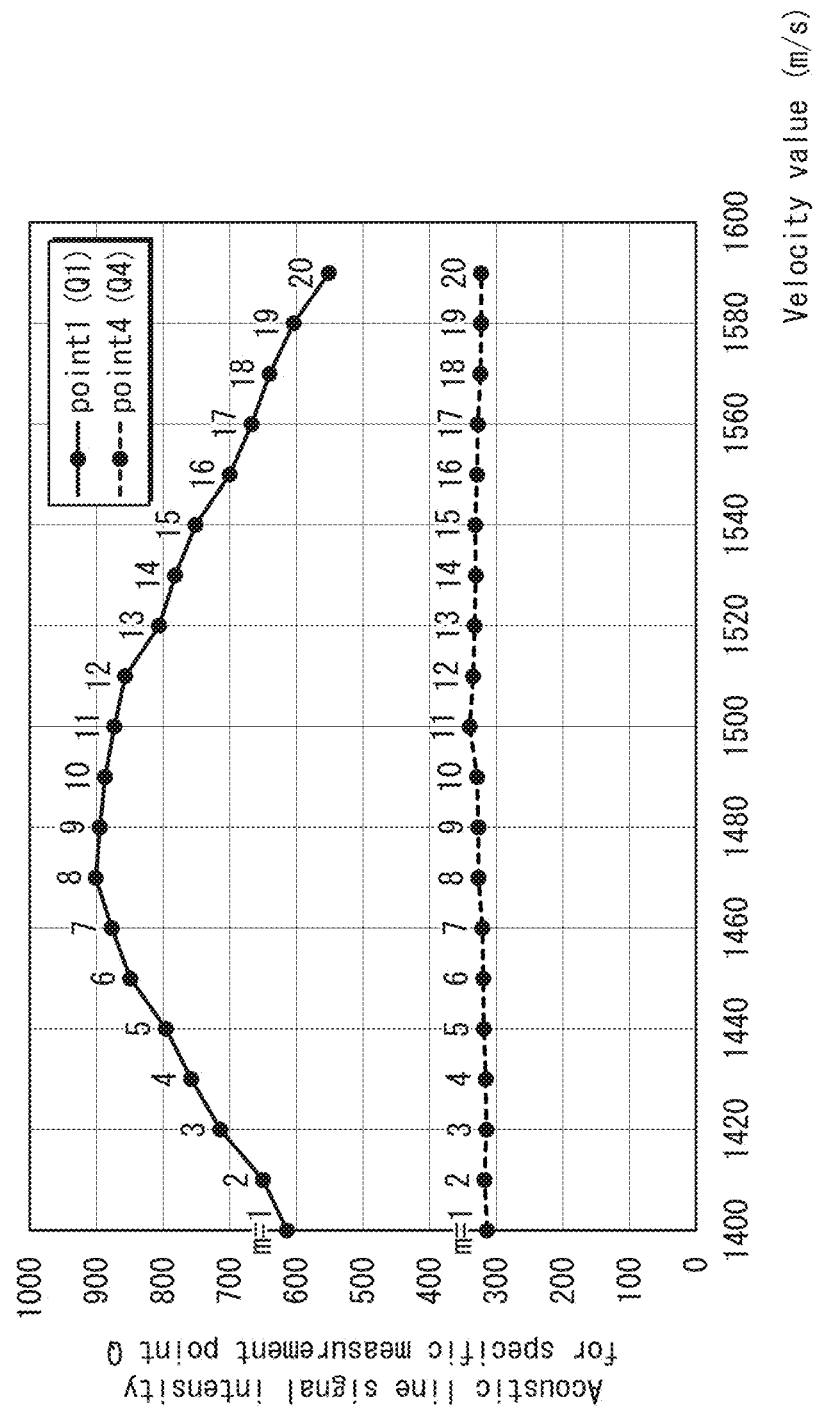
Figure 23:
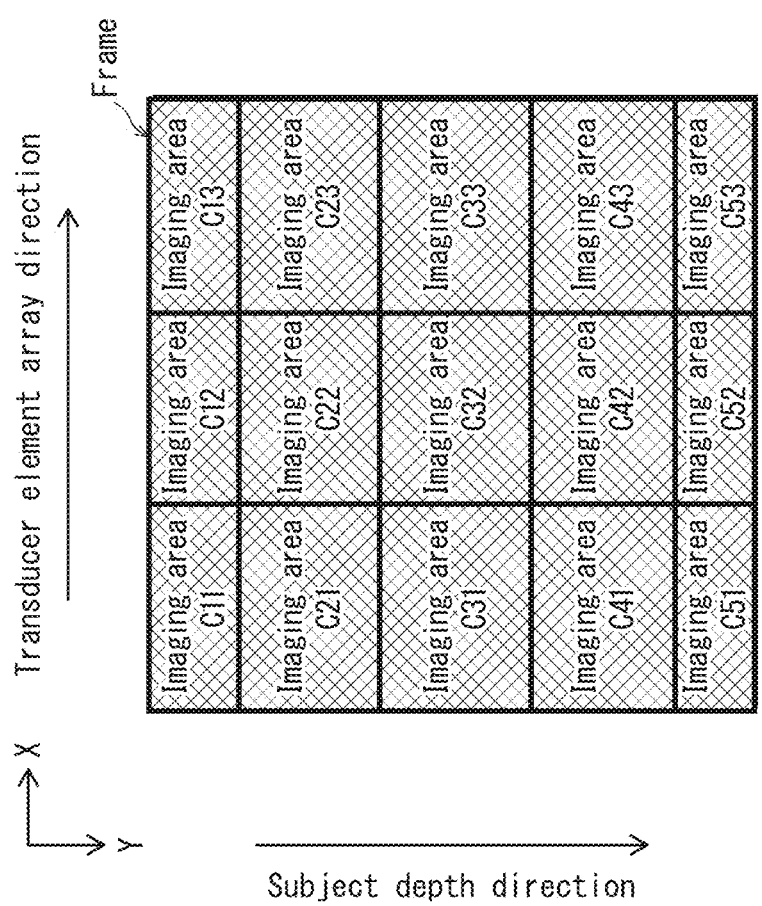
Figure 24:
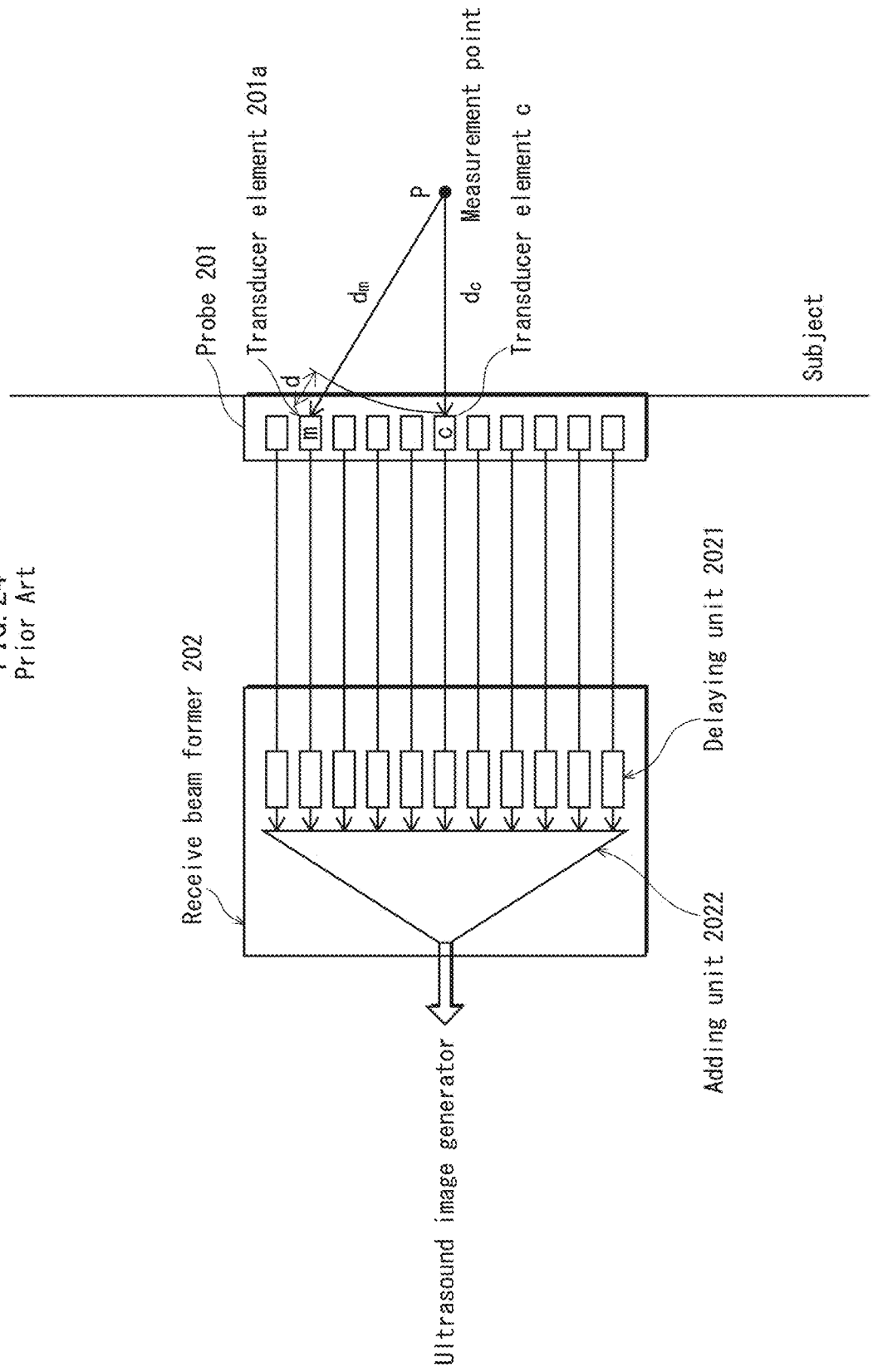
Figure 25B:
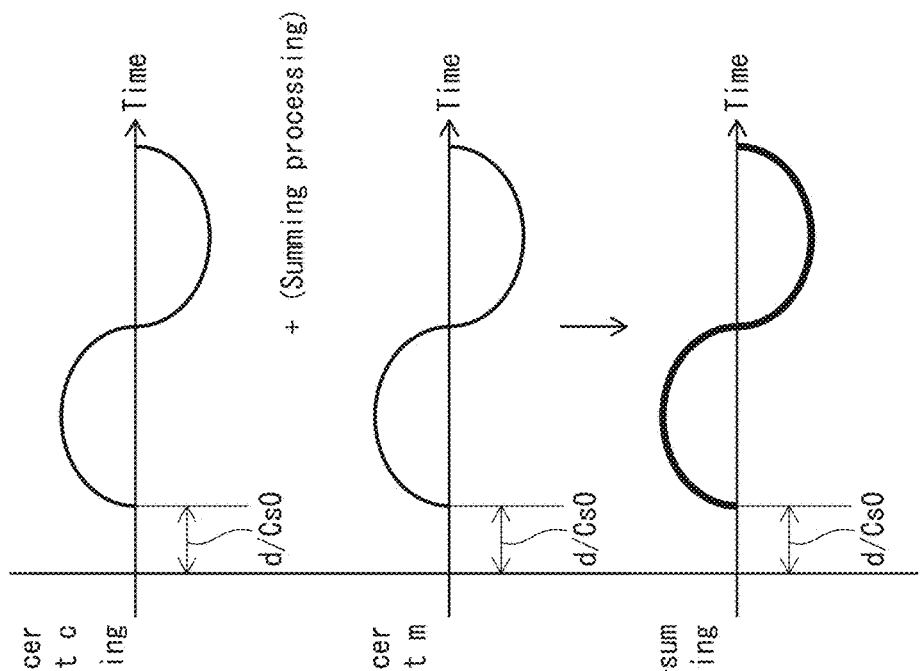
Figure 25A:
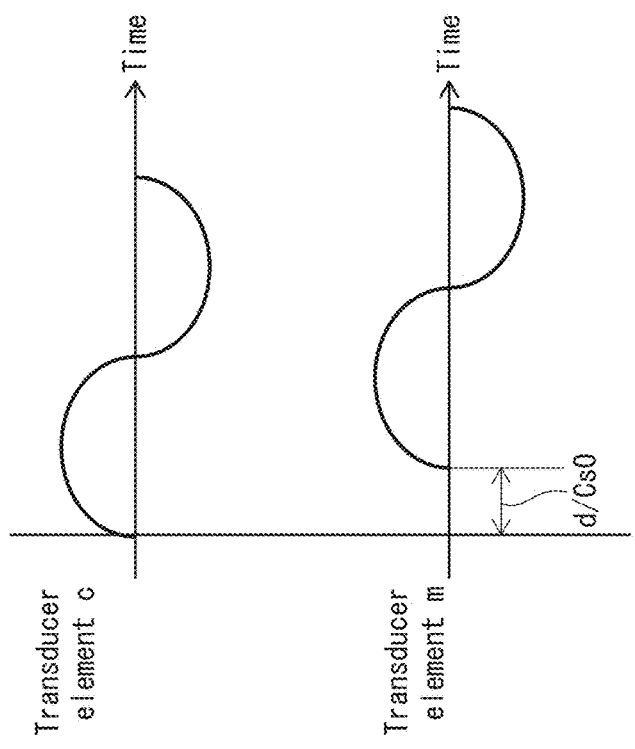

Each of FIGS. 19A and 19B shows a waveform of acoustic line signal intensities of measurement points located at the same depth as the specific measurement point, calculated by using the ultrasound diagnostic device 100 and based on different test velocity values, with FIG. 19A showing the results for a specific measurement point Q3 and FIG. 19B showing the results for a specific measurement point Q4;

FIG. 20 shows an ultrasound image used in the evaluation of changes in acoustic line signal intensity brought about by application of test velocity values, conducted by using the ultrasound diagnostic device 100;

FIG. 21 illustrates how acoustic line signal intensities for specific measurement points Q1 and Q4 in FIG. 20 change, when calculated by using the ultrasound diagnostic device 100 and based on different test velocity values;

Each of FIGS. 22A, 22B, and 22C shows the results of the evaluation of the appropriateness of the determination of the necessity of adjusting the velocity value, with FIG. 22A showing evaluation results for a tendon, FIG. 22B showing evaluation results for a cyst, and FIG. 22C showing evaluation results for white matter;

FIG. 23 is a schematic illustrating imaging areas Ci pertaining to a modification;

FIG. 24 is a schematic for explaining the operations of a receive beam former 202 in a conventional ultrasound signal processing device;

FIGS. 25A and 25B are schematics for explaining delay-and-sum processing in the conventional ultrasound signal processing circuit; and FIGS. 26A and 26B are schematics illustrating the influence of velocity difference in the delay-and-sum processing in the conventional ultrasound signal processing device.

DESCRIPTION OF THE PREFERRED EMBODIMENT

The following describes an embodiment of the technology pertaining to the present disclosure.

Embodiment

<Overall Structure>

The following describes an ultrasound diagnostic device 100 pertaining to the embodiment, with reference to the accompanying drawings.

Figure 1:
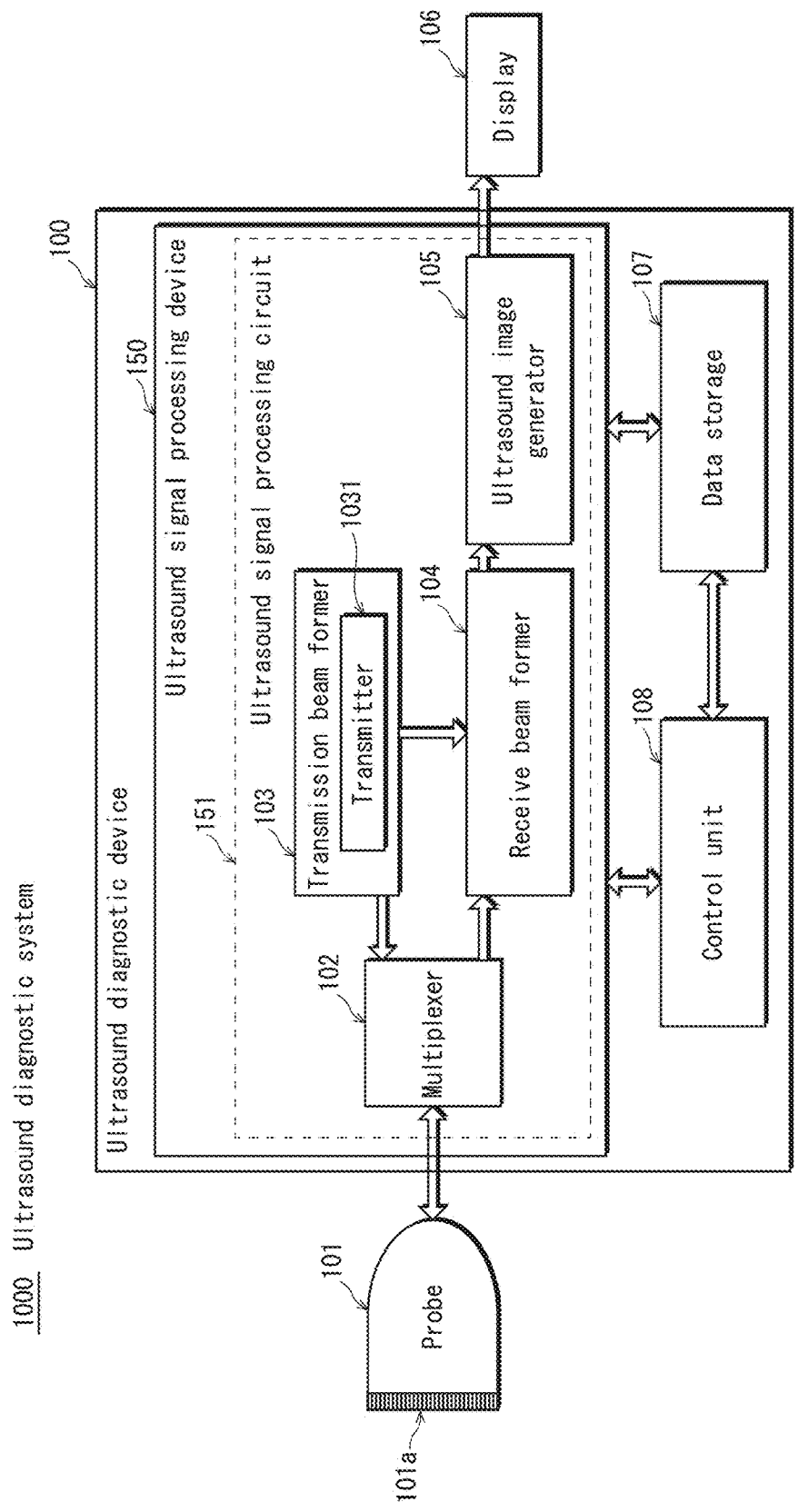
FIG. 1 is a functional block diagram illustrating the structure of an ultrasound diagnostic device 100 pertaining to an embodiment.

FIG. 1 illustrates functional blocks of an ultrasound diagnostic system 1000 pertaining to the embodiment. As illustrated in FIG. 1, the ultrasound diagnostic system 1000 includes: a probe 101; the ultrasound diagnostic device 100; and a display unit 106. The probe 101 includes a plurality of transducer elements 101a. The transducer elements 101a are disposed at a surface of a tip portion of the probe 101. Each of the transducer elements 101a transmits ultrasound towards the subject and receives reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102; a transmission beam former 103; and a receive beam former 104. The multiplexer 102 selects one or more of the transducer elements 101a for ultrasound transmission and one or more of the transducer elements 101a for ultrasound reception. The multiplexer 102 may select different ones of the transducer elements 101a for ultrasound transmission and ultrasound reception. Further, the multiplexer 102 provides the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The receive beam former 104 performs some amplification and A/D conversion on electric signals yielded by the transducer elements 101a for ultrasound reception, based on reflected ultrasound received by the probe 101, and performs receive beam forming to generate acoustic line signals. In addition, the ultrasound diagnostic device 100 includes: an ultrasound image generator 105; a data storage 107; and a control unit 108. The ultrasound image generator 105 generates an ultrasound image (a B-mode image) by performing processing such as envelope detection and logarithmic compression on acoustic line signals output from the receive beam former 104 to convert the acoustic line signals into luminance signals, and performing coordinate conversion on the luminance signals to obtain signals based on an orthogonal coordinate system. The data storage 107 stores the acoustic line signals output from the receive beam former 104 and the ultrasound image output from the ultrasound image generator 105. The control unit 108 controls each of the other constituent elements of the ultrasound diagnostic device 100.

Among the constituent elements of the ultrasound diagnostic device 100, the multiplexer 102, the transmission beam former 103, the receive beam former 104, and the ultrasound image generator 105 constitute an ultrasound signal processing circuit 151, and the ultrasound signal processing circuit 151 constitutes an ultrasound signal processing device 150.

Each constituent element of the ultrasound diagnostic device 100, for example, each of the multiplexer 102, the transmission beam former 103, the receive beam former 104, the ultrasound image generator 105, and the control unit 108 may be implemented by using a hardware circuit such as a field-programmable gate array (FPGA), an application-specific integrated circuit (ASIC), or the like. Alternatively, each of the constituent elements may be implemented by using a combination of software and a programmable device such as a central processing unit (CPU), a General-purpose computing on graphics processing unit (GPGPU), or any processor. Each of such constituent elements may be implemented as one circuit component, or as an aggregate of a plurality of circuit components. Further, a plurality of such constituent elements may be implemented by using one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, or a semiconductor memory. Alternatively, the data storage 107 may be an external storage device connected to the ultrasound diagnostic device 100.

Note that the ultrasound diagnostic device 100 pertaining to the embodiment need not have the structure illustrated in FIG. 1. For example, the ultrasound diagnostic device 100 need not include the multiplexer 102. Further, the probe 101 may have built-in therein a part or the entirety of each of the transmission beam former 103, the receive beam former 104, and the like.

<Structure of Main Part of Ultrasound Diagnostic Device 100>

The ultrasound diagnostic device 100 pertaining to the embodiment is characterized for the receive beam former 104, which performs computation with respect to electric signals acquired through the reception of reflected ultrasound by the probe 101, and generates acoustic line signals used in forming an ultrasound image. Accordingly, the present disclosure focuses on the structure and the functions of the receive beam former 104, and the structure and the functions of the transmission beam former 103, which causes the transducer elements 101a of the probe 101 to perform ultrasound transmission. Note that components other than the transmission beam former 103 and the receive beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the embodiment.

The following describes the structure of each of the transmission beam former 103 and the receive beam former 104.

1. Transmission Beam Former 103

The transmission beam former 103 is connected to the probe 101, via the multiplexer 102. However, note that the multiplexer 102 is not a mandatory element in the present disclosure. The transmission beam former 103 controls timings of application of high voltage with respect to each of a plurality of transducer elements 101a composing a transmission aperture Tx. The transmission aperture Tx is an array of transducer elements composed of all or some of the transducer elements 101a of the probe 101. Note that in the following, the term "transmission transducer element" is used to refer to transducer elements composing the transmission aperture Tx. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In the transmission processing, the transmitter 1031 performs focus processing so that ultrasound beams are appropriately focused. Specifically, the transmitter 1031 sets a delay amount for each transmission transducer element, and delays the transmission of the ultrasound beam from the transmission transducer element by the corresponding delay amount.

The transmitter 1031 repetitively performs ultrasound transmission while shifting the transmission aperture Tx in the transducer element array direction each time, so that all of the transducer elements 101a of the probe 101 transmit ultrasound. Further, each time ultrasound transmission has been completed, the transmitter 1031 outputs information indicating the positions of transmission transducer elements composing the transmission aperture Tx to the data storage 107, via the control unit 108. For example, supposing that the probe 101 has one hundred and ninety two (192) transducer elements 101a in total, the number of transmission transducer elements composing the transmission aperture Tx may be twenty (20) to one hundred (100). In the following, ultrasound transmission by the transmitter 1031, performed by using one transmission aperture (i.e., one set of transmission transducer elements of the predetermined number) is referred to as a transmission event.

Figure 2:
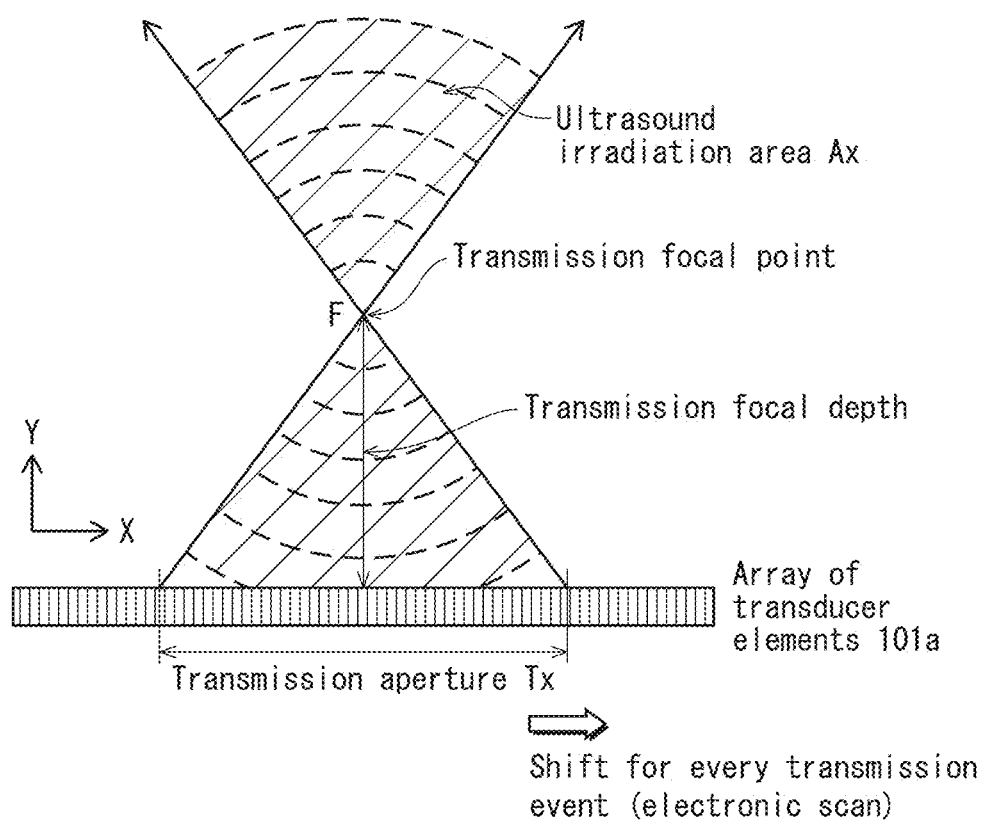
FIG. 2 is a schematic illustrating a propagation path of ultrasound transmitted from a transmission beam former 103.

FIG. 2 is a schematic illustrating a propagation path of an ultrasound beam formed by the transmission beam former 103. FIG. 2 illustrates a transmission aperture Tx for one transmission event (i.e., an array of transmission transducer elements 101a that contribute to ultrasound transmission in the transmission event).

The transmission beam former 103 controls ultrasound transmission by the transmission transducer elements such that a transmission transducer element closer to the center position of the transmission aperture Tx transmits ultrasound later in the transmission event. Due to this, a wavefront of ultrasound transmitted from the transmission transducer elements composing the transmission aperture Tx converges at one point at a certain focal depth in the subject (i.e., the transmission focal point F). Note that the depth of the transmission focal point F (i.e., focal depth) can be set as desired or required. After converging at the transmission focal point F, the wavefront of the transmitted ultrasound expands as before converging at the transmission focal point F. Thus, the transmitted ultrasound waves propagate through an hourglass-shaped area whose base is defined by the transmission aperture Tx and which is partitioned from other areas inside the subject by two straight lines intersecting at the transmission focal point F. In the following, the hourglass-shaped area described above, which is indicated by hatching in slanted lines in FIG. 2, is referred to as an ultrasound irradiation area Ax.

2. Receive Beam Former 104

Figure 3:
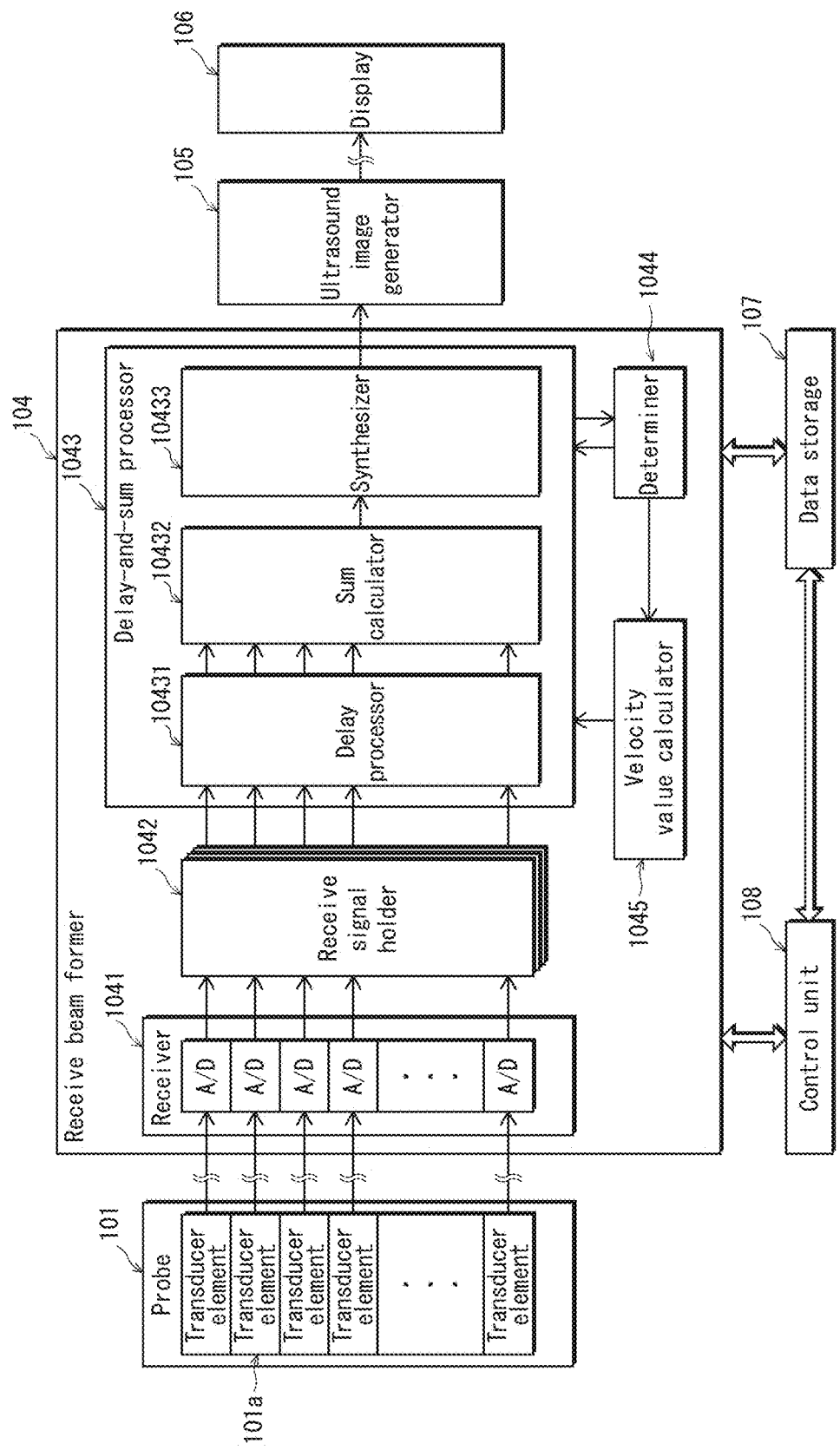
FIG. 3 is a functional block diagram illustrating the structure of a receive beam former 104 in the ultrasound diagnostic device 100.

The receive beam former 104 generates acoustic line signals from electric signals acquired by a plurality of transducer elements 101a. The transducer elements 101a acquire the electric signals based on reflected ultrasound received by the probe 101. Here, an acoustic line signal for one measurement point is generated by performing delay-and-sum processing with respect to receive signals from the measurement point. Description of the delay-and-sum processing is provided later in the present disclosure. FIG. 3 is a functional block diagram illustrating the structure of the receive beam former 104. As illustrated in FIG. 3, the receive beam former 104 includes: a receiver 1041; a receive signal holder 1042; a delay-and-sum processor 1043; a determiner 1044; and a velocity value calculator 1045.

The following describes the structure of each functional block of the receive beam former 104.

(1) Receiver 1041

The receiver 1041 is connected to the probe 101, via the multiplexer 102. However, note that the multiplexer 102 is not a mandatory element in the present disclosure. For each transmission event, the receiver 1040 generates receive signals (RF signals). The receiver 1040 generates the receive signals by first amplifying electric signals acquired by the probe 101 by receiving reflected ultrasound, and then performing A/D conversion on the amplified signals. The receiver 1041 performs the generation of receive signals for each transmission event performed in the order in which the transmission events are performed, and outputs the receive signals so generated to the receive signal holder 1042 to be stored in the receive signal holder 1042.

Here, the receiver 1041 generates one receive signal sequence (RF signal) for each of some or all of the transducer elements 101a of the probe 101. Specifically, a receive signal sequence for a given transducer element is a digital signal yielded by performing A/D conversion on an electrical signal yielded through conversion of reflected ultrasound received by the transducer element, and is a sequence of signals along the ultrasound transmission direction (corresponding to subject depth direction) that are received by the transducer element.

For each ultrasound transmission event, the receiver 1041 generates a receive signal sequence for each of some or all of the plurality of transducer elements 101a of the probe 101 that are specified by the multiplexer 102. Each of the transducer elements 101a for which the receiver 1041 generates a receive signal sequence is referred to in the following as a receive transducer element Ri. The generation of the receive signal sequence for a given receive transducer element Ri is based on reflected ultrasound yielded by the given receive transducer element Ri. In the embodiment, the receive transducer elements Ri are selected so that a center position of an array formed by the receive transducer elements Ri (referred to in the following as a receive aperture Rx) corresponds to a center position of the transmission aperture Tx, which is an array formed by the transmission transducer elements. Here, it is preferable that the number of receive transducer elements Ri be equal to or greater than the number of transmission transducer elements composing the transmission aperture Tx. Further, all of the transducer elements 101a of the probe 101 may be used as receive transducer elements Ri.

As already discussed above, the transmitter 1031 repetitively performs transmission events while shifting the transmission aperture Tx in the transducer element array direction each time, so that all of the transducer elements 101a of the probe 101 transmit ultrasound. Meanwhile, for each ultrasound transmission event, the receiver 1041 generates a receive signal sequence for each receive transducer element, and stores the receive signal sequences to the receive signal holder 1042.

(2) Receive Signal Holder 1042

The receive signal holder 1042 is a computer-readable recording medium. For example, the receive signal holder 1042 may be implemented by using a semiconductor memory. For each transmission event, the receive signal holder 1042 receives, from the transmitter 1031, a receive signal sequence for each receive transducer element. Further, the receive signal holder 1042 holds the receive signal sequences so received until one ultrasound image is generated. Alternatively, the receive signal holder 1042 may be implemented by using, for example, a hard disk, an MO, a DVD, or a DVD-RAM. Also, the receive signal holder 1042 may be an external storage device connected to the ultrasound diagnostic device 100. Alternatively, the receive signal holder 1042 may be implemented as a part of the data storage 107.

(3) Delay-and-Sum Processor 1043

The delay-and-sum processor 1043 is a circuit that generates an acoustic line signal for each of a plurality of measurement points that are included in a calculation-target area Bx. The delay-and-sum processor 1043 generates an acoustic line signal for a given measurement point included in the calculation-target area Bx by performing delay-and-sum processing with respect to receive signal sequences that the receive transducer elements have received from the measurement point. The calculation-target area Bx is a signal area that corresponds to an area within the subject and that is set for each transmission event. The calculation-target area Bx corresponding to a given transmission event is an area for which acoustic line signals are to be generated in response to the transmission event. Further, the delay-and-sum processor 1043 generates a frame acoustic line signal (i.e., a group of acoustic line signals corresponding to one frame) by generating an acoustic line signal for each measurement point included in each calculation-target area Bx, and combining acoustic line signals for a plurality of calculation-target areas Bx, each of which corresponding to one transmission event. Here, a frame is a unit of signals necessary for forming one ultrasound image. Further, one frame acoustic line signal is a combination of a plurality of acoustic line signals corresponding to one frame. In the embodiment, the calculation-target area Bx for a given transmission event, which is an area for which acoustic line signals are to be generated in response to the transmission event, is a linear area that has a width corresponding to one transducer element, that passes through a center position of the receive aperture Rx, and that is perpendicular to the transducer element array direction. However, the calculation target area Bx is not limited to such an area, and may be set as any area within the ultrasound irradiation area Ax.

As illustrated in FIG. 3, the delay-and-sum processor 1043 includes: a delay processor 10431; a sum calculator 10432; and a synthesizer 10433. The following describes the structure of each functional block of the delay-and-sum processor 1043.

Figure 4:
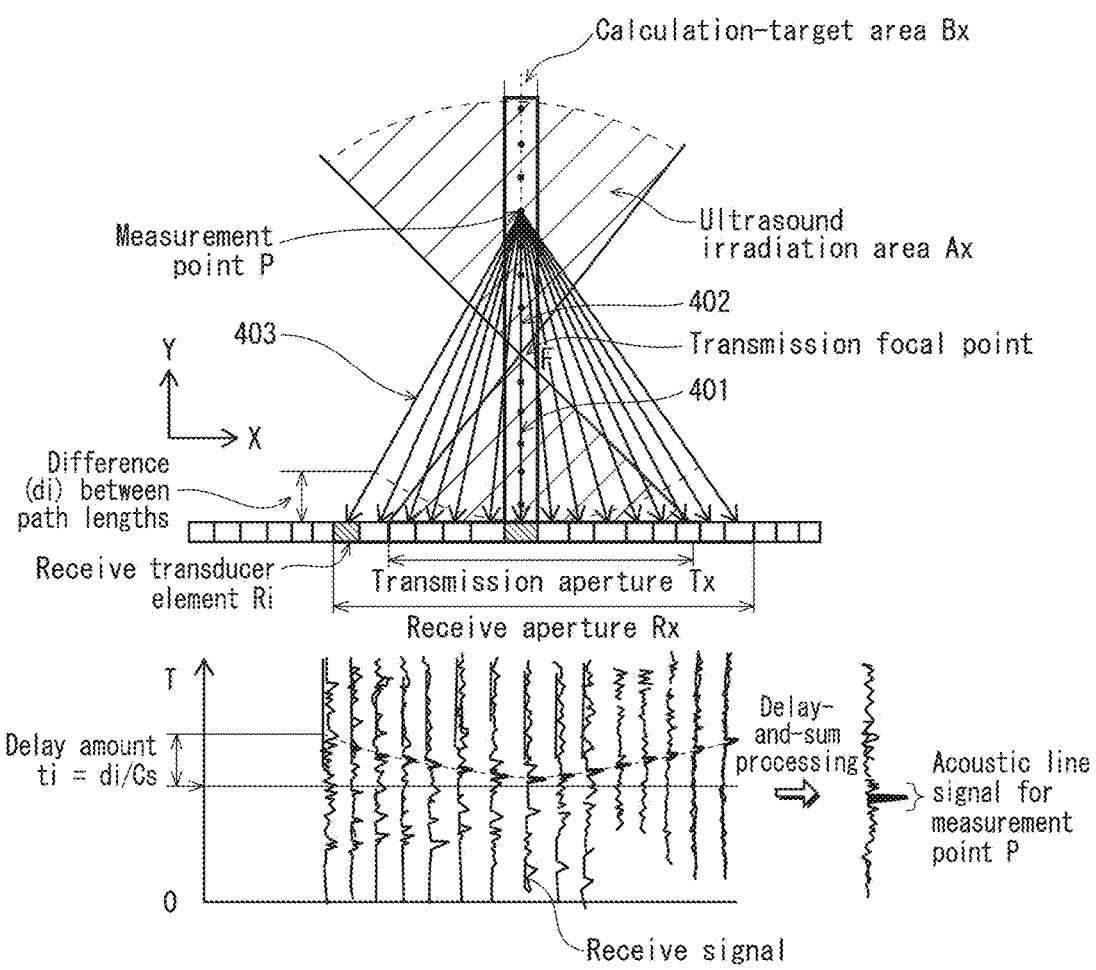
FIG. 4 is a schematic for explaining how an acoustic line signal for a measurement point P is generated.

FIG. 4 is a schematic for explaining how the delay-and-sum processor 1043 generates an acoustic line signal for a measurement point P. Following emission of ultrasound from the transmission aperture Tx, the wavefront of the ultrasound converges at the transmission focal point F after proceeding along path 401. Subsequently, the wavefront of the ultrasound expands and arrives at the measurement point P. When there is a change in acoustic impedance at the measurement point P, the transmitted ultrasound generates ultrasound reflection, which is received by each receive transducer element Ri of the receive aperture Rx. Here, the length of path 401+402 leading to the measurement point P via the transmission focal point F is geometrically calculable. Further, the length of path 403 for each receive transducer element Ri, which is a path from the measurement point P to the receive transducer element Ri, is also geometrically calculable.

i) Delay Processor 10431

The delay processor 10431 specifies, from among a receive signal sequence corresponding to the receive transducer element Ri, a receive signal that the receive transducer element Ri receives based on reflected ultrasound from the measurement point P. The delay processor 10431 performs this processing for each receive transducer element Ri included in the receive aperture Rx, and for each of a plurality of measurement points P included in the calculation-target area Bx. Specifically, the delay processor 10431 specifies a receive signal corresponding to the measurement point P for the receive transducer element Ri by taking into account a delay amount corresponding to the receive transducer element Ri, which is a delay with which reflected ultrasound arrives at the receive transducer element Ri and is calculated by dividing a relative difference in distance from the measurement point P by a velocity value Cs. Note that a velocity value Cs is output by the velocity value calculator 1045 for each imaging area Ci. An imaging area Ci is an area within the subject and is a group of measurement points P for which the same velocity value Cs is applied. The setting of imaging areas Ci and velocity values Cs for the respective imaging areas Ci are described later in the present disclosure.

As illustrated in FIG. 4, the delay processor 10431 geometrically calculates, for each measurement point P, the lengths of paths from the measurement point P to the respective receive transducer elements Ri, based on information indicating the positions of the receive transducer elements Ri and information indicating the positions of the measurement points P. The delay processor 10431 performs this processing for each transmission event. Further, for each of the receive transducer elements Ri, the delay processor 10431 calculates a delay amount (indicated by "ti" in FIG. 4). The delay amount for a given receive transducer element Ri indicates the delay with which reflected ultrasound from the measurement point P arrives at the receive transducer element Ri, and is calculated by dividing a relative difference in path length from the measurement point P (indicated by "di" in FIG. 4) by the velocity value Cs. Further, for each of the receive transducer elements Ri, the delay processor 10431 specifies, from the receive signal sequence for the receive transducer element Ri, a receive signal that is in accordance with the delay amount for the receive transducer element Ri as a receive signal based on reflected ultrasound from the measurement point P. For each measurement point P included in the calculation-target area Bx, the delay processor 10431 calculates delay amounts for the respective receive transducer elements Ri and specifies receive signals for the respective receive transducer elements Ri.

ii) Sum Calculator 10432

The sum calculator 10432 is a circuit that generates a delayed-and-summed acoustic line signal for each measurement point P. Specifically, the sum calculator 10432 receives, from the delay processor 10431, specified receive signals corresponding to the measurement point P for the respective receive transducer elements Ri, and sums together the specified receive signals so received. Further, in generating an acoustic line signal for each measurement point P, the sum calculator 10432 may multiply a specified receive signal for each receive transducer element Ri by a weight corresponding to the receive transducer element Ri that is included in a weight sequence (reception apodization weight) composed of weights set with respect to the respective receive transducer elements Ri, and sum the weighted receive signals for the respective receive transducer elements Ri. When using such a weight sequence, it is preferable that the weight sequence be composed of weights distributed symmetrically with respect to the transmission focal point F, such that the maximum weight is set with respect to the receive transducer element located at a center position of the receive aperture Rx in the transducer element array direction. As the shape of distribution of the weights indicated by the weight sequence, any shape is applicable, including but not limited to a hamming window, a hanning window, and a rectangular window.

For each measurement point P, the sum calculator 10432 sums the receive signals for the receive transducer elements Ri, after the receive signals have been put in the same phase by the delay processor 10431. Due to this, the sum calculator 10432 is capable of extracting receive signals for the measurement point P while increasing S/N ratio by summing the receive signals for the measurement point P received by the receive transducer elements Ri based on reflected ultrasound from the measurement point P.

As a result of one transmission event and processing accompanying the transmission event, an acoustic line signal is generated for each of the measurement points P included in the calculation-target area Bx for the transmission event. Further, by repetitively performing transmission events while gradually shifting the transmission aperture Tx in the transducer element array direction each time, all of the transducer elements 101a in the probe 101 perform ultrasound transmission. Due to this, a set of acoustic line signals corresponding to the calculation-target area Bx is generated for each transmission event, and is output to the synthesizer 10433 for each transmission event.

iii) Synthesizer 10433

The synthesizer 10433 is a circuit that generates a frame acoustic line signal by combining acoustic line signal sets each corresponding to the calculation-target area Bx of a different transmission event. Specifically, for each transmission event, the synthesizer 10433 receives as input a set of acoustic line signals generated for the respective measurement points P included in the calculation-target area Bx for the transmission event. Further, the synthesizer 10433 generates a frame acoustic line signal by combining acoustic line signals that are generated in response to different transmission events, based on the positions of the measurement points P. As already discussed above, ultrasound transmission is performed by repetitively performing transmission events while gradually shifting the transmission transducer element array (i.e., the transmission aperture Tx) in the transducer element array direction each time. Due to this, the position of the calculation-target area Bx, which is set based on a corresponding transmission event, also shifts in the transducer element array direction from one transmission event to another. Thus, by combining acoustic line signals that are generated in response to different transmission events, a frame acoustic line signal covering calculation-target areas Bx of all transmission events can be generated.

The synthesizer 10433 outputs the frame acoustic line signal so generated to the determiner 1044 and the ultrasound image generator 105.

(4) Determiner 1044

The determiner 1044 is a circuit that, for each imaging area Ci, performs a determination of a necessity of adjusting a velocity value Cs for the imaging area Ci. A velocity value Cs for a given imaging area Ci is a velocity value that is used in delay-and-sum processing related to the measurement points included in the imaging area Ci, and the same velocity value Cs is applied uniformly to all measurement points included in the imaging area Ci. Specifically, the determiner 1044 performs this determination based on an acoustic line signal intensity of a specific measurement point Qi in the imaging area Ci, and acoustic line signal intensities of at least some measurement points in the image area Ci. Note that the specific measurement point Qi in a given imaging area Ci is one of the measurement points included in the imaging area Ci that is selected based on acoustic line signal intensities of at least some measurement points included in the imaging area Ci. Further, in the present disclosure, an acoustic line signal intensity of a measurement point refers to an intensity of an acoustic line signal generated from the measurement point.

Figure 5:
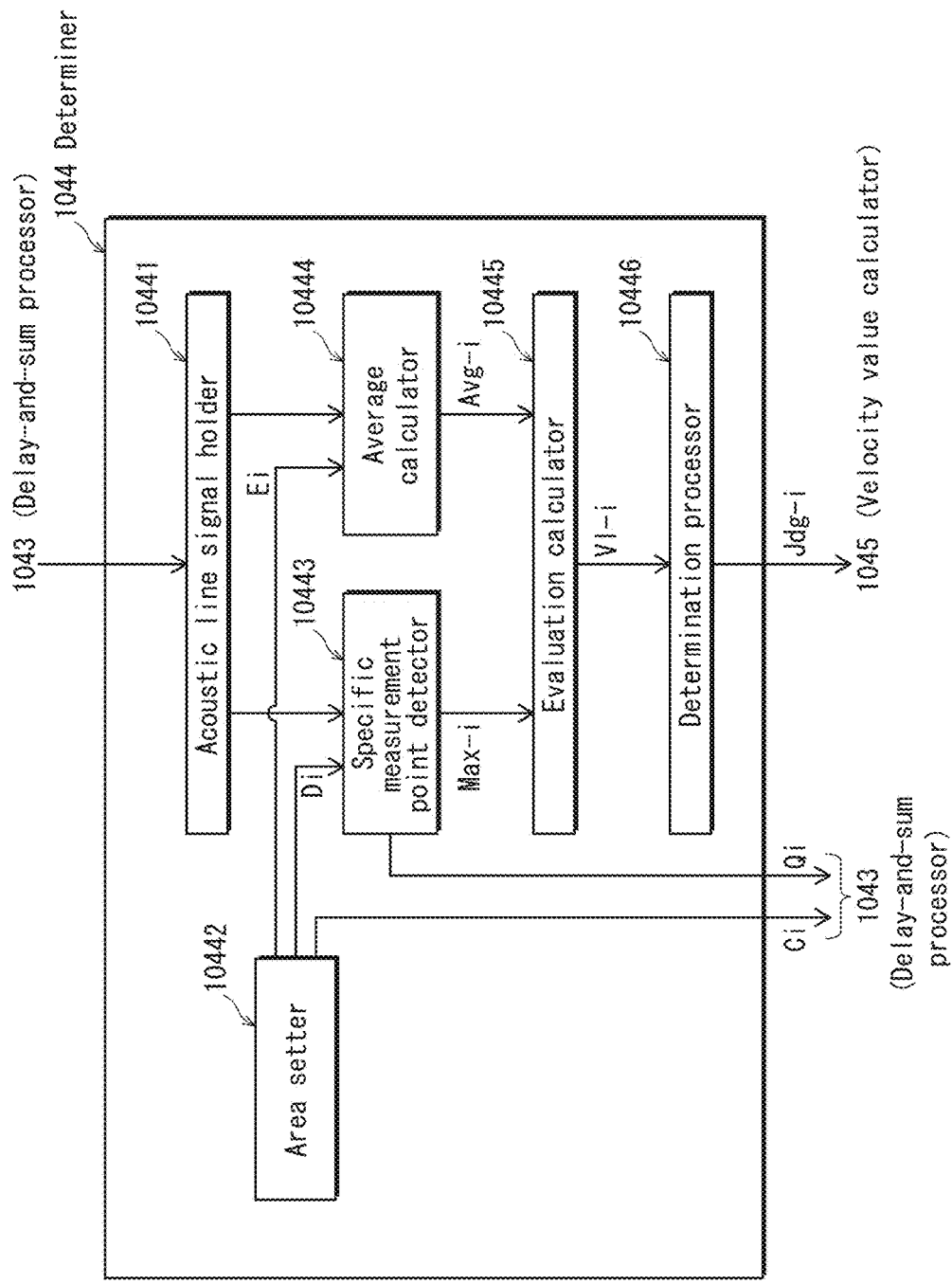
FIG. 5 is a functional block diagram illustrating the structure of a determiner 1044 in the ultrasound diagnostic device 100.

FIG. 5 is a functional block diagram illustrating the structure of the determiner 1044. As illustrated in FIG. 5, the determiner 1044 includes: an acoustic line signal holder 10441; an area setter 10442; a specific measurement point detector 10443; an average calculator 10444; an evaluation calculator 10445; and a determination processor 10446. The following describes the structure of each functional block of the determiner 1044.

i) Acoustic Line Signal Holder 10441

The acoustic line signal holder 10441 is a computer-readable recording medium. For example, the acoustic line signal holder 10441 may be implemented by using a semiconductor memory. The acoustic line signal holder 10441 receives and holds therein one frame acoustic line signal (i.e., a set of acoustic line signals corresponding to one frame) generated and output by the delay-and-sum processor 1043.

ii) Area Setter 10442

The area setter 10442 sets multiple types of areas within the frame indicated by the frame acoustic line signal held by the acoustic line signal holder 10441. Each of the multiple types of areas is used in the determination of the necessity of velocity value adjustment. Further, in the present disclosure, a frame is an area for which an ultrasound image is rendered. The multiple types of areas set by the area setter 10442 are described in the following.

Figure 6:
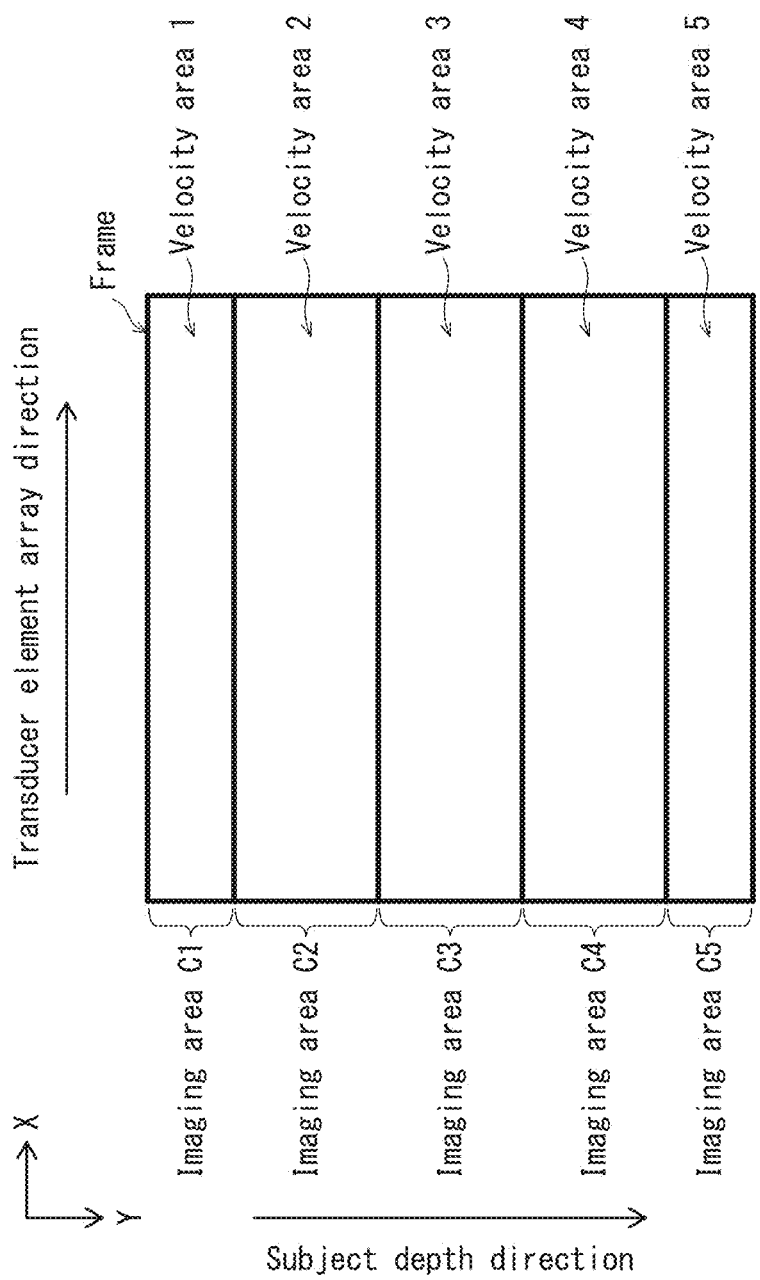
FIG. 6 is a schematic illustrating imaging areas Ci (i being variable between 1, 2, 3, 4, and 5), for each of which the determiner 1044 conducts a determination of a necessity of adjusting a velocity value.

FIG. 6 is a schematic illustrating imaging areas Ci (i being variable between 1, 2, 3, 4, and 5). The determiner 1044 performs the determination of the necessity of velocity value adjustment for each imaging area Ci. Each imaging area Ci is the maximum of a corresponding search area Di (i being variable between 1, 2, 3, 4, and 5) that is an area in which the search for the specific measurement point Qi in the imaging area Ci is performed. Specifically, in the embodiment, the imaging areas Ci in one frame are acquired by dividing the frame along the subject depth direction. Further, information indicating the positions of the respective imaging areas Ci having been set are output to the delay-and-sum processor 1043.

Figure 7:
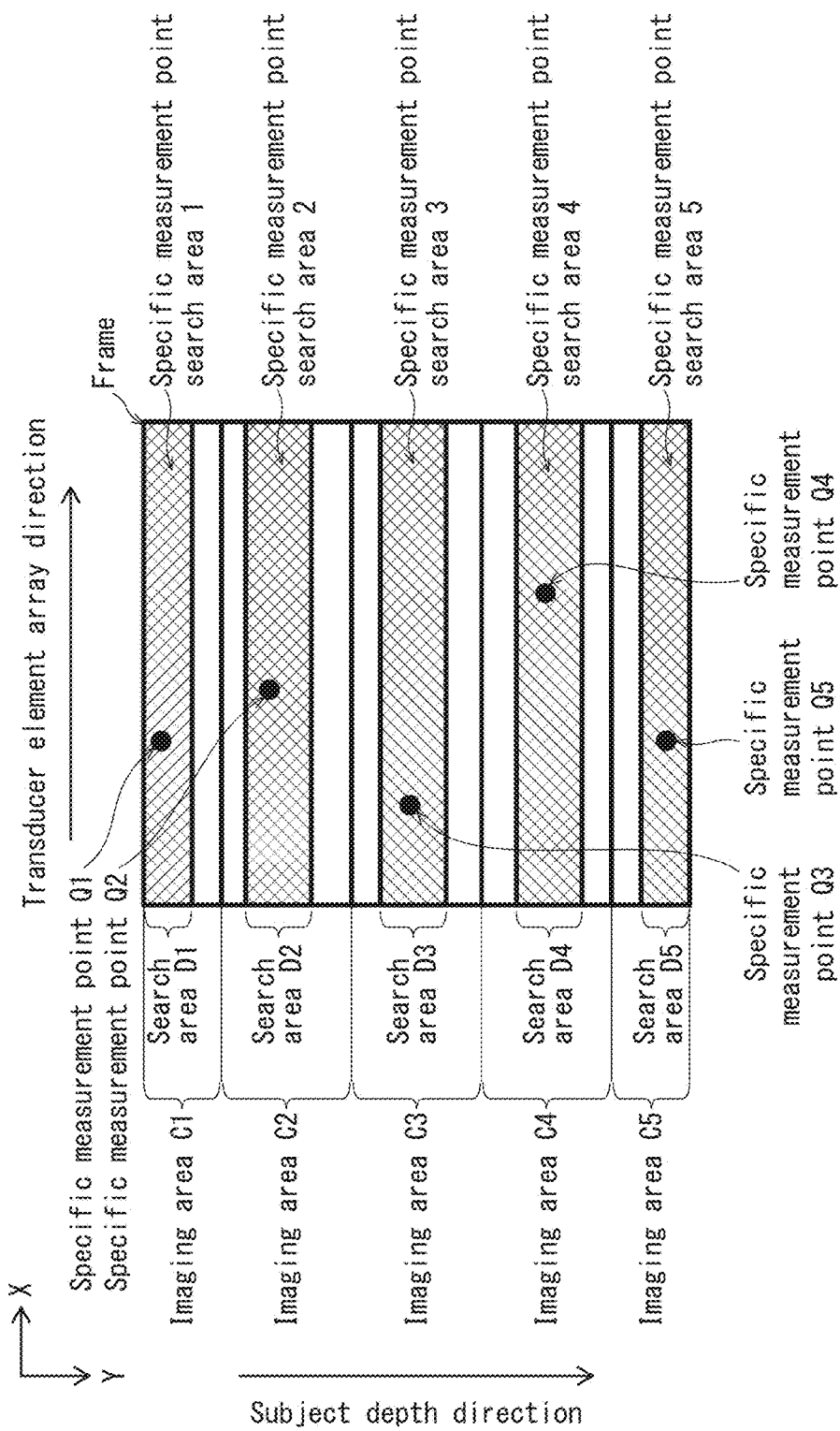
FIG. 7 is a schematic illustrating search areas Di (i being variable between 1, 2, 3, 4, and 5), in each of which the determiner 1044 conducts a search for a specific measurement point used in the determination of the necessity of adjusting the velocity value.

FIG. 7 is a schematic illustrating the search areas Di (i being variable between 1, 2, 3, 4, and 5). As already described above, each search area Di is an area in which the search for the specific measurement point Qi in the corresponding imaging area Ci is performed. Specifically, a specific measurement point Qi (i being variable between 1, 2, 3, 4, and 5) for each imaging area Ci is one of the measurement points included in the corresponding search area Di that is selected based on acoustic line signals of the respective measurement points included in the search area Di. In the embodiment, one measurement point having greatest acoustic line signal intensity among the measurement points included in each search area Di is selected as the specific measurement point Qi in the corresponding imaging area Ci. However, the specific measurement point Qi need not be selected in such a manner. Alternatively, one measurement point among the measurement points included in each search area Di whose acoustic line signal indicates highest luminance, maximal intensity, maximal luminance, or the like may be selected as the specific measurement point Qi in the corresponding imaging area Ci.

Specifically, in the embodiment, each search area Di is acquired by removing, from a corresponding imaging area Ci, an area of the imaging area Ci that is located near a boundary between the imaging area Ci and an adjacent imaging area Ci. The search areas Di are set in such a manner in order to prevent specific measurement points Qi detected from different imaging areas Ci from being located undesirably close to one another. Further, the area setter 10442 outputs information indicating the positions of the respective search areas Di having been set to the specific measurement point detector 10443.

Figure 8:
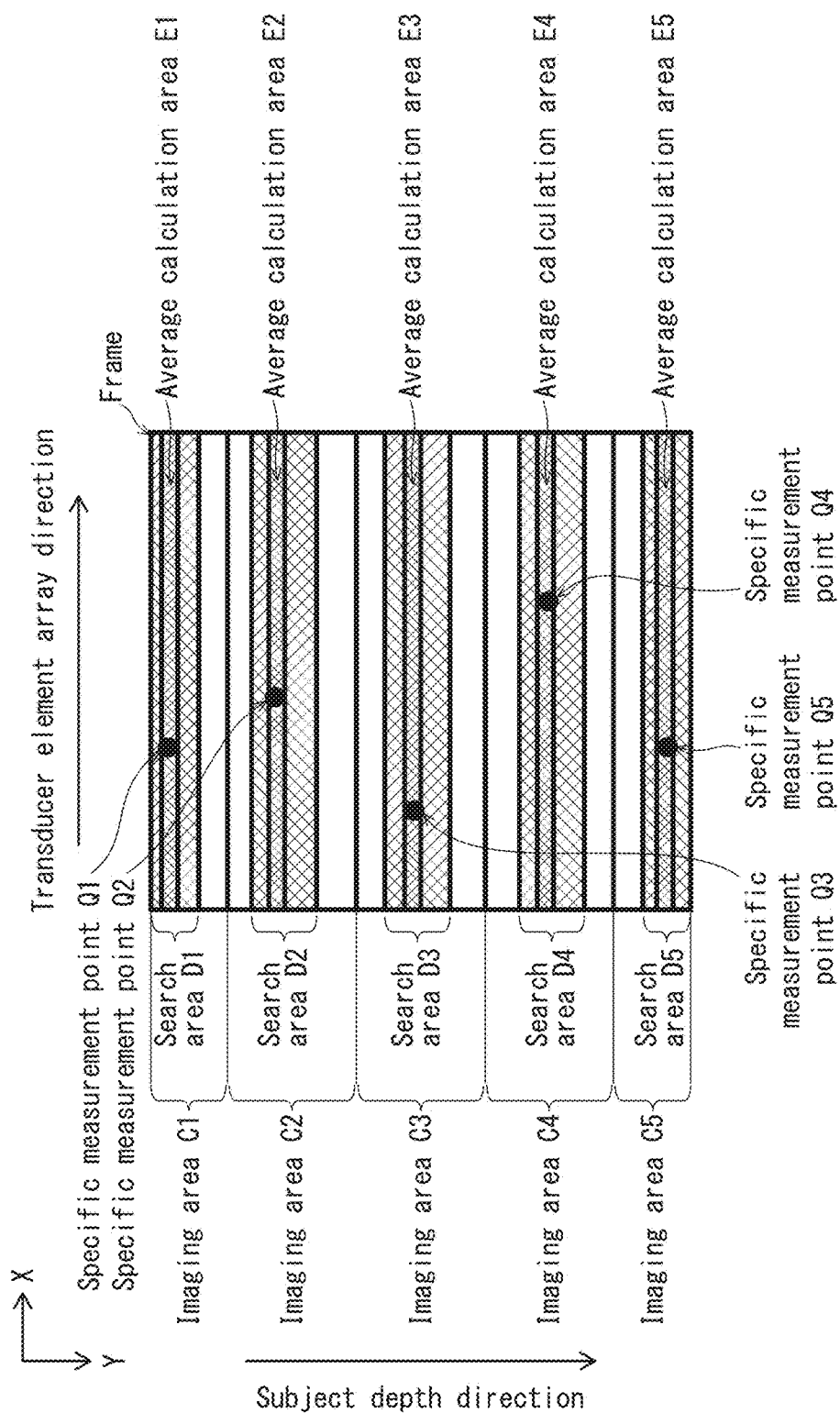
FIG. 8 is a schematic illustrating average calculation areas Ei (i being variable between 1, 2, 3, 4, and 5), based on each of which the determiner 1044 calculates an average acoustic line signal intensity within a corresponding imaging area Ci, used in the determination of the necessity of adjusting the velocity value.

FIG. 8 is a schematic illustrating average calculation areas Ei (i being variable between 1, 2, 3, 4, and 5). Each average calculation area Ei corresponds to one imaging area Ci, and is an area including a plurality of measurement points from which average acoustic line signal intensity for the corresponding imaging area Ci is calculated. The average acoustic line signal intensity for each imaging area Ci is used in the determination of the necessity of velocity value adjustment with respect to the imaging area Ci. Specifically, in the embodiment, average acoustic line signal intensity is calculated by calculating the arithmetic mean of acoustic line signal intensities. However, average acoustic line signal intensity may be calculated through a different method. For example, instead of calculating an arithmetic mean of acoustic line signal intensities, a median or a mode of acoustic line signal intensities within the average calculation area Ei may be calculated as the average acoustic line signal intensity for the corresponding imaging area Ci.

Further, in the embodiment, the measurement points composing each average calculation area Ei (i.e., the measurement points based on which the average acoustic line signal intensity for the corresponding imaging area Ci is calculated) correspond to ones of the measurement points included in the corresponding imaging area Ci that are located at the same subject depth as the specific measurement point Qi in the imaging area Ci. Thus, in the embodiment, each average calculation area Ei is a linear area that includes the specific measurement point Qi in the corresponding imaging area Ci and that is parallel to the transducer element array direction. However, the average calculation areas Ei need not be set in such a manner. For example, each average calculation area Ei may be set as an area having any shape within the corresponding imaging area Ci, as long as the average calculation area Ei includes the specific measurement point Qi in the corresponding imaging area Ci and a proximal area of the specific measurement point Qi. That is, each average calculation area Ei is an area having any shape that is included in the corresponding imaging area Ci and that includes the specific measurement point of the corresponding imaging area Ci. For example, each average calculation area Ei may be an area that has a predetermined width and that includes ones of the measurement points of a corresponding imaging area Ci that are located on a virtual line indicating the same subject depth as the specific measurement point Qi in the corresponding imaging area Ci or within a predetermined distance from the virtual line. Alternatively, each average calculation area Ei may be an area that includes ones of the measurement points of a corresponding imaging area Ci that are located within a predetermined distance from the specific measurement point Qi in the corresponding imaging area Ci. Further, the area setter 10442 outputs information indicating the positions of the respective average calculation areas Ei having been set to the average calculator 10444.

In particular, when using one measurement point that has maximum luminance among measurement points included in each search area Di as the specific measurement point Qi in a corresponding imaging area Ci, it is preferable that average luminance of acoustic line signals be used in place of average intensity of acoustic line signals.

iii) Specific Measurement Point Detector 10443

Referring to FIG. 5 once again, the specific measurement point detector 10443 detects the specific measurement point Qi in each imaging area Ci by comparing the acoustic line signal intensities of the respective measurement points included in a corresponding search area Di and searching for one of the measurement points included in the corresponding search area Di that has maximum acoustic line signal intensity. Specifically, the specific measurement point detector 10443 receives as input the information indicating the positions of the respective search areas Di from the area setter 10442. Further, based on the frame acoustic line signal held by the acoustic line signal holder 10441, the specific measurement point detector 10443 searches for acoustic line signals of measurement points that are located within each search area Di. Further, the specific measurement point detector 10443, for each search area Di, detects one of the measurement points included in the search area Di that has the maximum acoustic line signal intensity as the specific measurement point Qi in a corresponding imaging area Ci. In addition, the specific measurement point detector 10443 outputs information indicating the position of the specific measurement point Qi to the delay-and-sum processor 1043, and outputs the acoustic line signal intensity Max−i of the specific measurement point Qi to the evaluation calculator 10445.

iv) Average Calculator 10444

The average calculator 10444 calculates, for each imaging area Ci, an average Avg−i based on the acoustic line signal intensities of the respective measurement points included within the corresponding average calculation area Ei. Specifically, the average calculator 10444 receives as input the information indicating the positions of the respective average calculation areas Ei from the area setter 10442. Further, based on the frame acoustic line signal held by the acoustic line signal holder 10441, the average calculator 10444 searches for acoustic line signals of measurement points that are located within each average calculation area Ei. Further, the average calculator 10441, for each imaging area Ci, calculates the average Avg-i by calculating the average acoustic line signal intensity within the corresponding average calculation area Ei. In addition, the average calculator 10444 outputs the average Avg-i to the evaluation calculator 10445.

v) Evaluation Calculator 10445

For each imaging area Ci, the evaluation calculator 10445 calculates an evaluation Vl-i to be used in the determination of the necessity of adjusting the velocity value Cs for the imaging area Ci. In calculating the evaluation Vl-i for each imaging area Ci, the evaluation calculator 10445 receives as input the acoustic line signal intensity Max-i of the specific measurement point Qi in the imaging area Ci from the specific measurement point detector 10443 and receives as input the average Avg-i for the imaging area Ci from the average calculator 10444. Further, the evaluation calculator 10445 calculates the evaluation Vl-i for the imaging area Ci by using Equation 1.

$$\text{Evaluation} = \frac{\text{Acoustic line signal intensity of specific measurement point specified in search area}}{\text{Average of acoustic line signal intensities within average calculation area}} \quad \text{[Equation 1]}$$

Alternatively, the evaluation calculator 10445 may calculate the evaluation Vl-i for the imaging area Ci by using Equation 2.

$$\text{Evaluation} = \frac{\text{Acoustic line signal intensity of specific measurement point specified in imaging area}}{\text{Average of acoustic line signal intensities within imaging area}} \quad \text{[Equation 2]}$$

Further, the evaluation calculator 10445 outputs the evaluation Vl-i for the imaging area Ci to the determination processor 10446.

vi) Determination Processor 10446

The determination processor 10446, for each imaging area Ci, performs the determination of the necessity of adjusting the velocity value Cs for the imaging area Ci. Specifically, in performing the determination for each imaging area Ci, the determination processor 10446 receives as input the evaluation Vl-i for the imaging area Ci output from the evaluation calculator 10445. The determination processor 10446 determines that adjusting a velocity value Cs-i (i being variable between 1, 2, 3, 4, and 5) for an imaging area Ci is necessary when the evaluation Vl-i for the imaging area Ci is equal to or higher than a predetermined reference value, and determines that adjusting the velocity value Cs-i for the imaging area Ci is unnecessary when the evaluation Vl-i for the imaging area Ci is lower than the predetermined reference value. Further, the determination processor 10446 outputs a determination result Jdg-i for the imaging area Ci to the velocity value calculator 1045.

(5) Velocity Value Calculator 1045

Referring once again to FIG. 3, the velocity value calculator 1045 is a circuit that, for each imaging area Ci, calculates the velocity value Cs-i for the imaging area Ci, and outputs the velocity value Cs-i to the delay-and-sum processor 1043.

Figure 9:
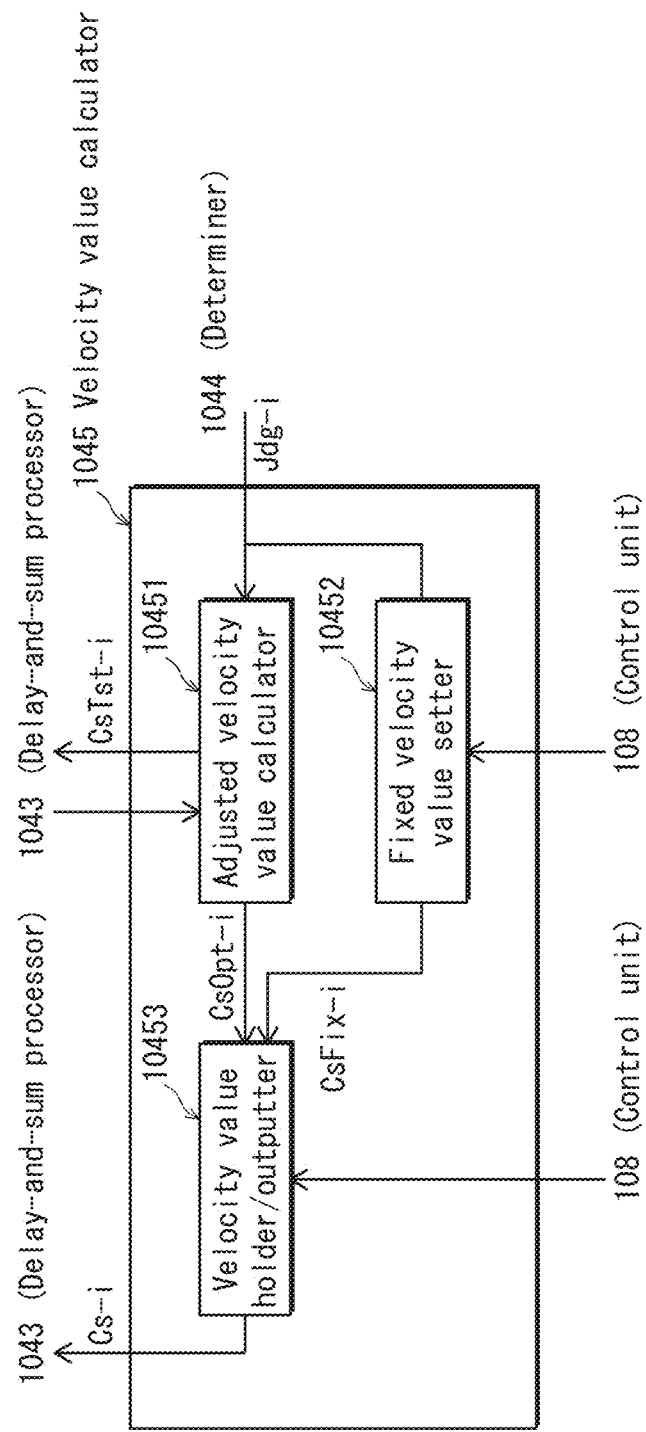
FIG. 9 is a functional block diagram illustrating the structure of a velocity value calculator 1045 in the ultrasound diagnostic device 100.

FIG. 9 is a functional block diagram illustrating the structure of the velocity value calculator 1045 of the ultrasound diagnostic device 100. The velocity value calculator 1045 includes: an adjusted velocity value calculator 10451; a fixed velocity value setter 10452; and a velocity value holder/outputter 10453. The following describes the structure of each functional block of the velocity value calculator 1045.

i) Adjusted Velocity Value Calculator 10451

The adjusted velocity value calculator 10451, when the determiner 1044 determines that adjustment of the velocity value Cs-i for a given imaging area Ci is necessary, calculates an adjusted velocity value CsOpt-i for the imaging area Ci by using an acoustic line signal of the specific measurement point Qi in the imaging area Ci, and outputs the adjusted velocity value CsOpt-i for the imaging area Ci to the velocity value holder/outputter 10453. Information indicating the position of the specific measurement point Qi in the imaging area Ci is output from the determiner 1044 to the delay-and-sum processor 1043. Note that the method for calculating the adjusted velocity value CsOpt-i is described later in the present disclosure.

ii) Fixed Velocity Value Setter 10452

The fixed velocity value setter 10452, when the determiner 1044 determines that adjustment of the velocity value Cs-i for a given imaging area Ci is unnecessary, sets a fixed velocity value CsFix-i (second fixed value) as the velocity value for the imaging area Ci, and outputs the fixed velocity value CsFix-i to the velocity value holder/outputter 10453. In addition, when the delay-and-sum processor 1043 is to perform delay-and-sum processing for calculating provisional acoustic line signals to be used for detecting the specific measurement point Qi in a given imaging area Ci, the fixed velocity value setter 10452 sets the fixed velocity value CsFix-i (first fixed value) as the velocity value for the imaging area Ci, and outputs the fixed velocity value CsFix-i to the velocity value holder/outputter 10453. Here, it is preferable that the fixed velocity value CsFix-i indicate a possible value of ultrasound velocity within the human body, or more specifically, a value within a range of no smaller than 1525 m/s and no greater than 1545 m/s. In the embodiment, the fixed velocity value CsFix-i is a velocity value of 1540 m/s, which is considered as a standard ultrasound velocity in the human body. However, the fixed velocity value CsFix-i may take values other than 1540 m/s. For example, for an imaging area Ci located between two imaging areas Ci+1 and Ci-1, a velocity value Cs-i+1 applied to the imaging area Ci+1 or a velocity value Cs-i-1 applied to the imaging area Ci-1 may be applied as the fixed velocity value CsFix-i for the imaging area Ci.

Alternatively, for an imaging area Ci located between two imaging areas Ci+1 and Ci-1, an average or the like of a velocity value Cs-i+1 applied to the imaging area Ci+1 and a velocity value Cs-i-1 applied to the imaging area Ci-1 may be applied as the fixed velocity value CsFix-i for the imaging area Ci.

Further, for an imaging area Ci located at an end of a row of imaging areas, or in other words, for an imaging area Ci only having one imaging area adjacent thereto (imaging area Ci+1 or imaging area Ci-1), a velocity value applied to the adjacent imaging area (velocity value Cs-i+1 or velocity value Cs-i-1) may be applied as the fixed velocity value CsFix-i for the imaging area Ci.

iii) Velocity Value Holder/outputter 10453

Figure 10:
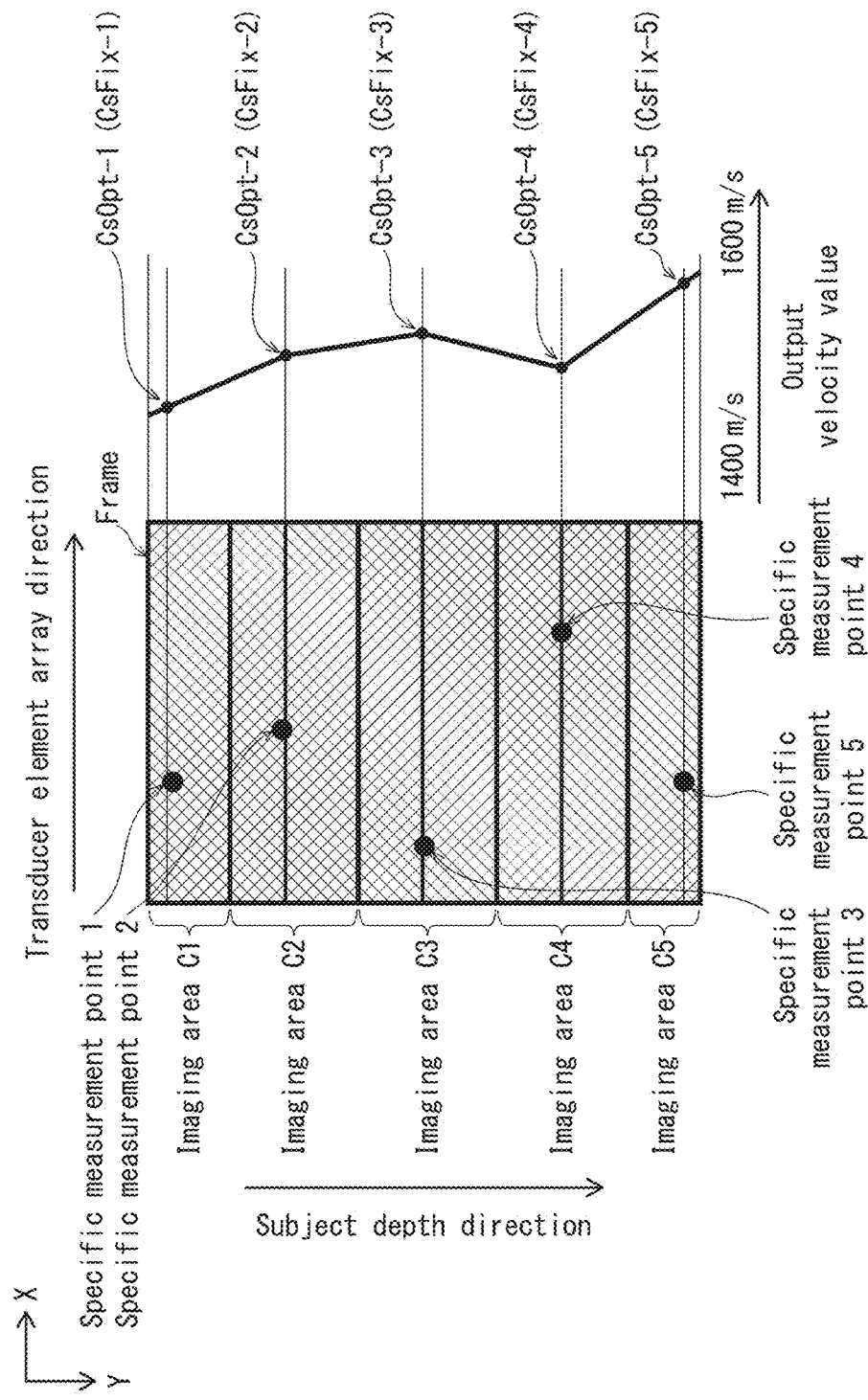
FIG. 10 is a schematic illustrating velocity values output by a velocity value holder/outputter 10453.

The velocity value holder/outputter 10453 holds the velocity values Cs−i for the respective imaging areas Ci. Further, the velocity value holder/outputter 10453 outputs the velocity values Cs−i to the delay-and-sum processor 1043 based on instructions from the control unit 108. FIG. 10 is a schematic illustrating velocity values output by the velocity value holder/outputter 10453.

The velocity value Cs−i that the velocity value holder/outputter 10453 holds for a given imaging area Ci is either an adjusted velocity value CsOpt−i (i being variable between 1, 2, 3, 4, and 5) calculated by the adjusted velocity value calculator 10451 or the fixed velocity value CsFix−i (i being variable between 1, 2, 3, 4, and 5) set by the fixed velocity value setter 10452. The velocity value holder/outputter 10453 stores the velocity value Cs−i for the imaging area Ci until one ultrasound image is generated. Further, the velocity value holder/outputter 10453 performs depth-direction linear interpolation by using the velocity values Cs−i for the respective imaging areas Ci. Thus, the velocity value holder/outputter 10453 is capable of calculating continuous velocity values corresponding to respective depth-direction subject positions, and to output such velocity values to the delay-and-sum processor 1043.

(6) Details of Adjusted Velocity Value Calculator 10451

Figure 11:
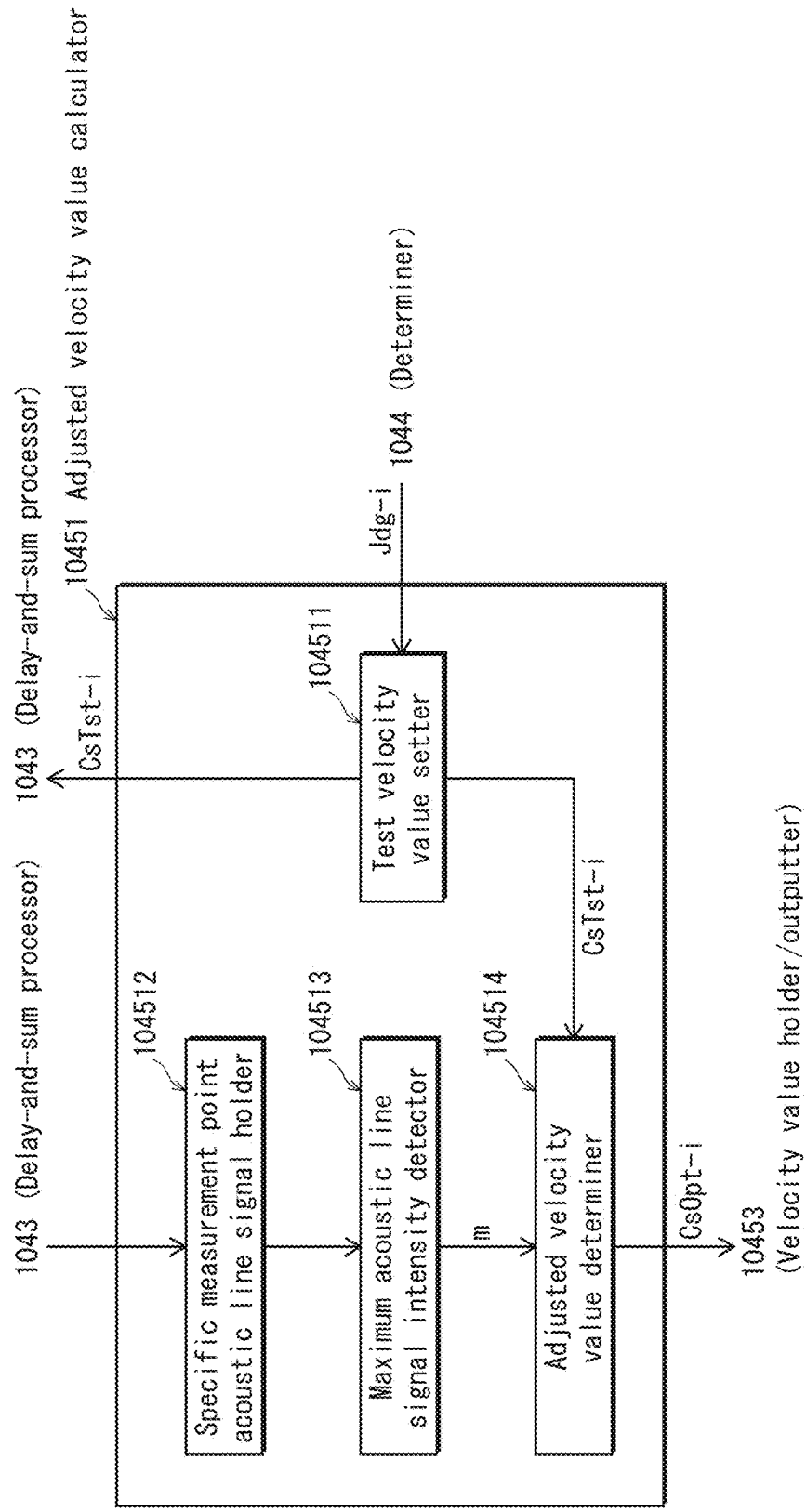
FIG. 11 is a functional block diagram illustrating the structure of an adjusted velocity value calculator 10451 in the ultrasound diagnostic device 100.
Figure 12:
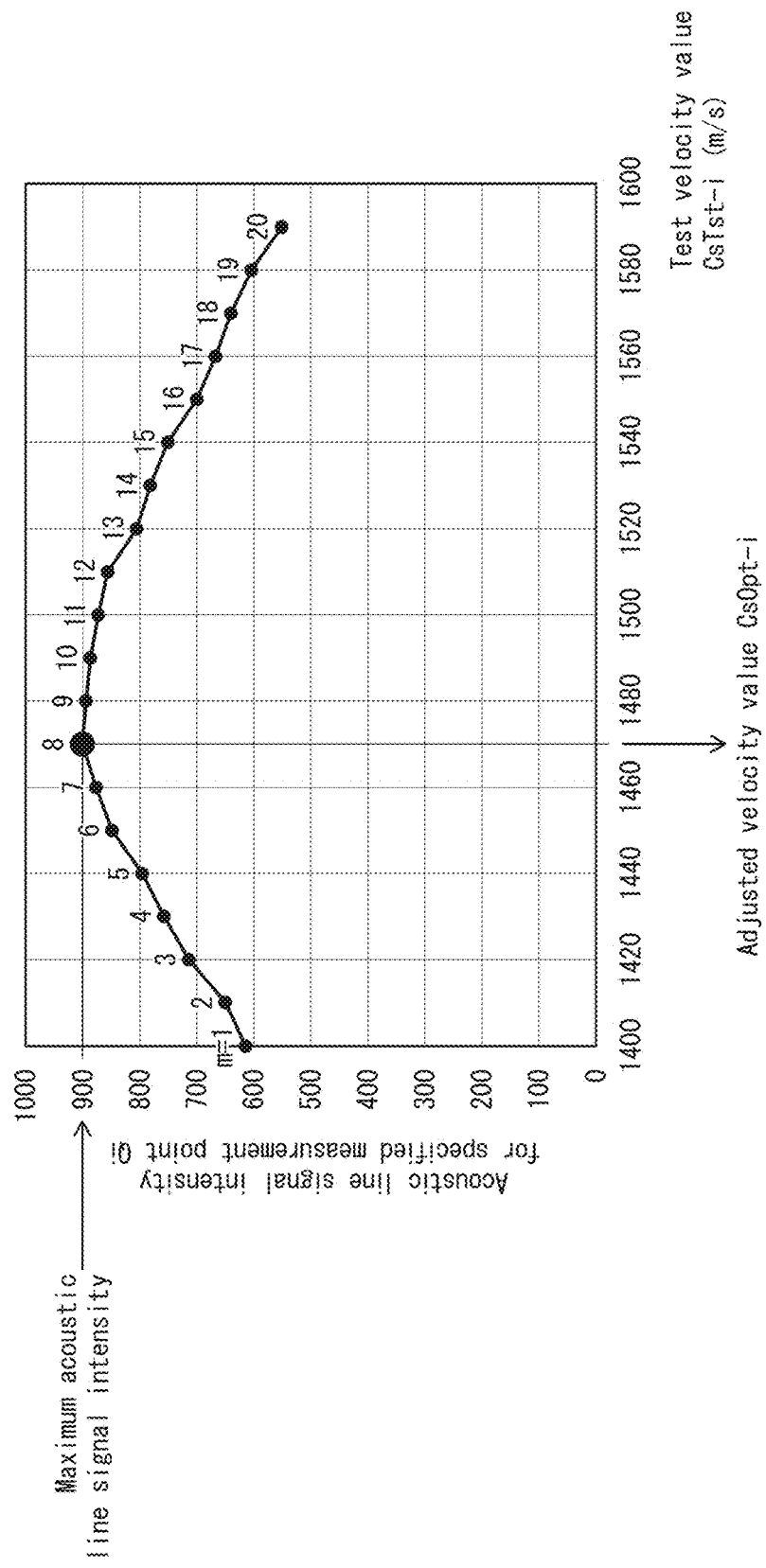
FIG. 12 is a schematic illustrating how the adjusted velocity value calculator 10451 calculates an adjusted velocity value.

The following describes the adjusted velocity value calculator 10451 in detail. FIG. 11 is a functional block diagram illustrating the structure of the adjusted velocity value calculator 10451. FIG. 12 is a schematic illustrating how the adjusted velocity value calculator 10451 calculates an adjusted velocity value.

As illustrated in FIG. 11, the adjusted velocity value calculator 10451 includes: a test velocity value setter 104511; a specific measurement point acoustic line signal holder 104512; a maximum acoustic line signal intensity detector 104513; and an adjusted velocity value determiner 104514.

The test velocity value setter 104511, when acquiring from the determiner 1044 a determination result Jdg−i indicating necessity of adjusting the velocity value Cs−i for a given imaging area Ci, outputs test velocity values CsTst−i to the delay-and-sum processor 1043. Here, the test velocity values CsTst−i are velocity values to be used in delay-and-sum processing for calculating provisional acoustic line signals for detecting the maximum acoustic line signal intensity of the specific measurement point Qi in the imaging area Ci. FIG. 12 illustrates an example of the test velocity values CsTst−i. In the embodiment, the test velocity values CsTst−i include twenty (20) velocity values (one velocity value for each m, where m is variable between 1, 2, 3, 4, 5, 6, 7, 8, 9, 10, 11, 12, 13, 14, 15, 16, 17, 18, 19, and 20) differing from one another by 10 m/s. Further, the test velocity values CsTst−i are within the range from 1400 m/s to 1590 m/s, inclusive.

The delay-and-sum processor 1043, based on the test velocity values CsTst−i and the information indicating the position of the specific measurement point Qi in the imaging area Ci, which is output from the determiner 1044, generates provisional acoustic line signals for the specific measurement point Qi by performing delay-and-sum processing by using the respective test velocity values CsTst−i. Further, the delay-and-sum processor 1043 outputs the provisional acoustic line signals so generated to the specific measurement point acoustic line signal holder 104512.

The specific measurement point acoustic line signal holder 104512 holds the provisional acoustic line signals generated and output by the delay-and-sum processor 1043.

The maximum acoustic line signal intensity detector 104513 detects a provisional acoustic line signal having maximum intensity among the provisional acoustic line signals held by the specific measurement point acoustic line signal holder 104512, and outputs, to the adjusted velocity value determiner 104514, identification information m identifying one of the test velocity values CsTst−i yielding the provisional acoustic line signal having maximum intensity. Upon receiving the identification information m from the maximum acoustic line signal intensity detector 104513, the adjusted velocity value determiner 104514 determines the test velocity value CsTst−i yielding the provisional acoustic line signal having maximum intensity as the adjusted velocity value CsOpt−i for the imaging area Ci. The adjusted velocity value determiner 104514 outputs the adjusted velocity value CsOpt−i to the velocity value holder/outputter 10453.

Here, the test velocity value CsTst−i yielding the provisional acoustic line signal having maximum intensity is determined as the adjusted velocity value CsOpt−i. This configuration is made since, by using a velocity value suiting the examination-target position (i.e., an adjusted velocity value), appropriate delay-and-sum processing can be performed with respect to receive signals based on reflected ultrasound from a measurement point, and thus, acoustic line signal intensity of the measurement point can be increased.

<Operations>

The following describes the operations of the ultrasound diagnostic device 100 having the structure described up to this point.

1. Overall Operation in Ultrasound Examination

Figure 13:
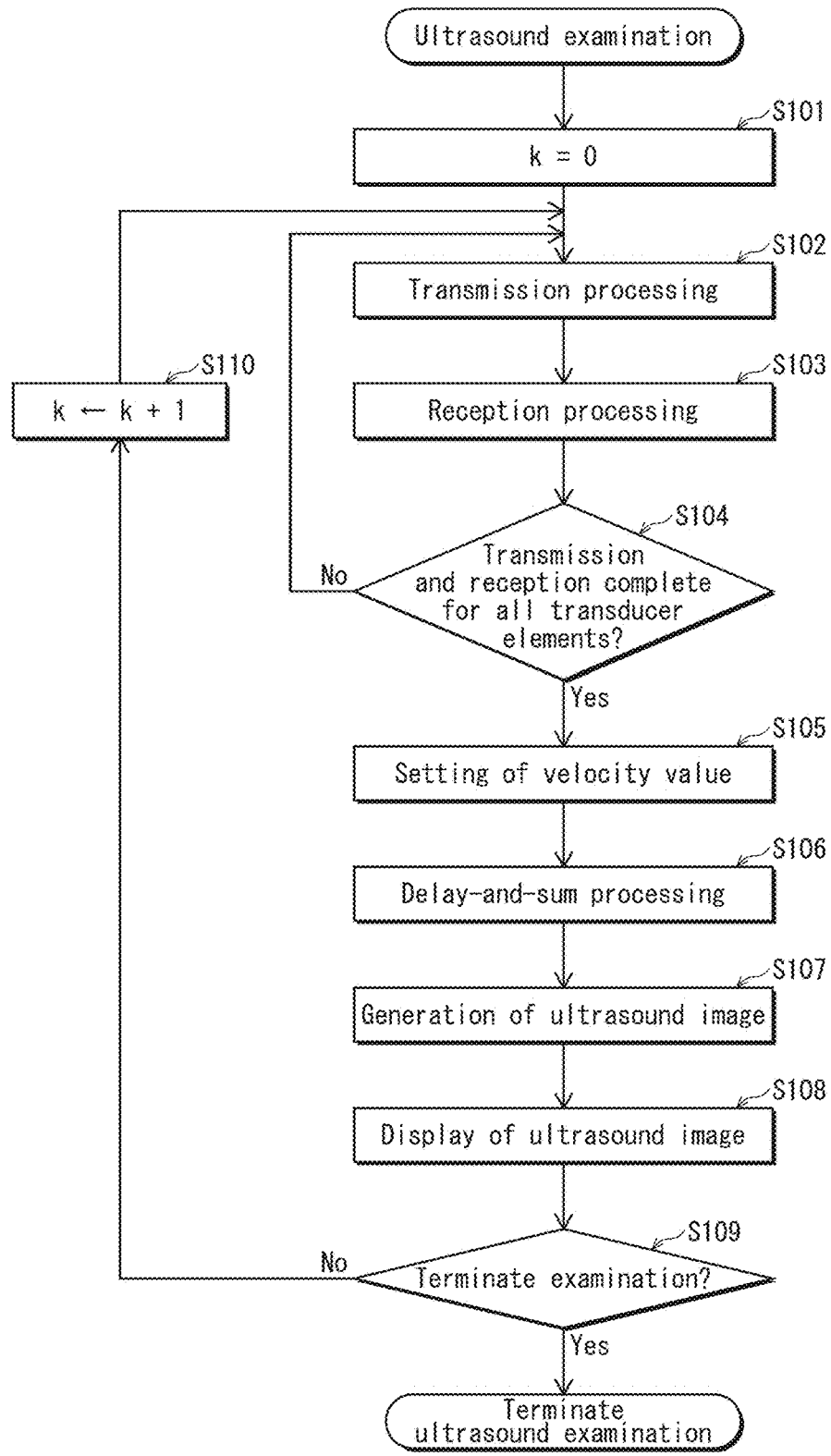
FIG. 13 is a flowchart illustrating the operations of the ultrasound diagnostic device 100 in ultrasound examination.

FIG. 13 is a flowchart illustrating the operations of the ultrasound diagnostic device 100 in ultrasound examination.

First, value k is initialized before the initial generation of a frame ultrasound image following the commencement of ultrasound examination (Step S101).

In Step S102, the transmitter 1031 performs transmission processing (a transmission event) of supplying a transmission signal causing transmission of an ultrasound beam to each transmission transducer element of the transmission aperture Tx.

In Step S103, the receiver 1041 generates receive signals based on electric signals yielded through the reception of reflected ultrasound by the probe 101, and outputs the receive signals to be stored in the receive signal holder 1042. Then, a determination is made of whether or not all transducer elements 101a of the probe 101 have performed ultrasound transmission (S104). When one or more of the transducer elements 101a have not yet performed ultrasound transmission, processing returns to Step S102, which results in another transmission event being executed by using the next transmission aperture Tx in the transducer element array direction. Meanwhile, when all of the transducer elements 101a have performed ultrasound transmission, processing proceeds to Step S105.

In Step S105, the velocity value calculator 1045 sets a velocity value Cs−i for each imaging area Ci in the frame for which an ultrasound image is to be generated, and outputs the velocity value Cs−i to the delay-and-sum processor 1043. The velocity setting processing (processing in Step S105) is described in detail later in the present disclosure.

In Step S106, the delay-and-sum processor 1043 performs delay-and-sum processing for each measurement point included in the frame, and thereby generates an acoustic line signal for each measurement point included in the frame. Thus, the delay-and-sum processor 1043 generates one frame acoustic line signal. Specifically, the delay-and-sum processor 1043 generates an acoustic line signal for a given measurement point by performing delay-and-sum processing with respect to receive signal sequences that the respective receive transducer elements have received from the measurement point, by using the velocity value Cs−i set to the imaging area Ci including the measurement point.

In Step S107, the ultrasound image generator 105 generates an ultrasound image (a B-mode image) corresponding to the frame by performing processing such as envelope detection and logarithmic compression on the acoustic line signals included in the frame acoustic line signal output from the delay-and-sum processor 1043 to convert the acoustic line signals into luminance signals, and performing coordinate conversion on the luminance signals to obtain signals based on an orthogonal coordinate system.

In Step S108, the display unit 106 displays, on a display screen, the ultrasound image corresponding to the frame, which is output from the ultrasound image generator 105. Subsequently, a determination is made of whether or not input for terminating examination has been performed (Step S109). When input for terminating examination has not been performed, the value of k is incremented (Step S110) before processing returns to Step S101. Meanwhile, when input for terminating examination has been performed, ultrasound examination is terminated.

2. Velocity Setting Processing

Figure 14:
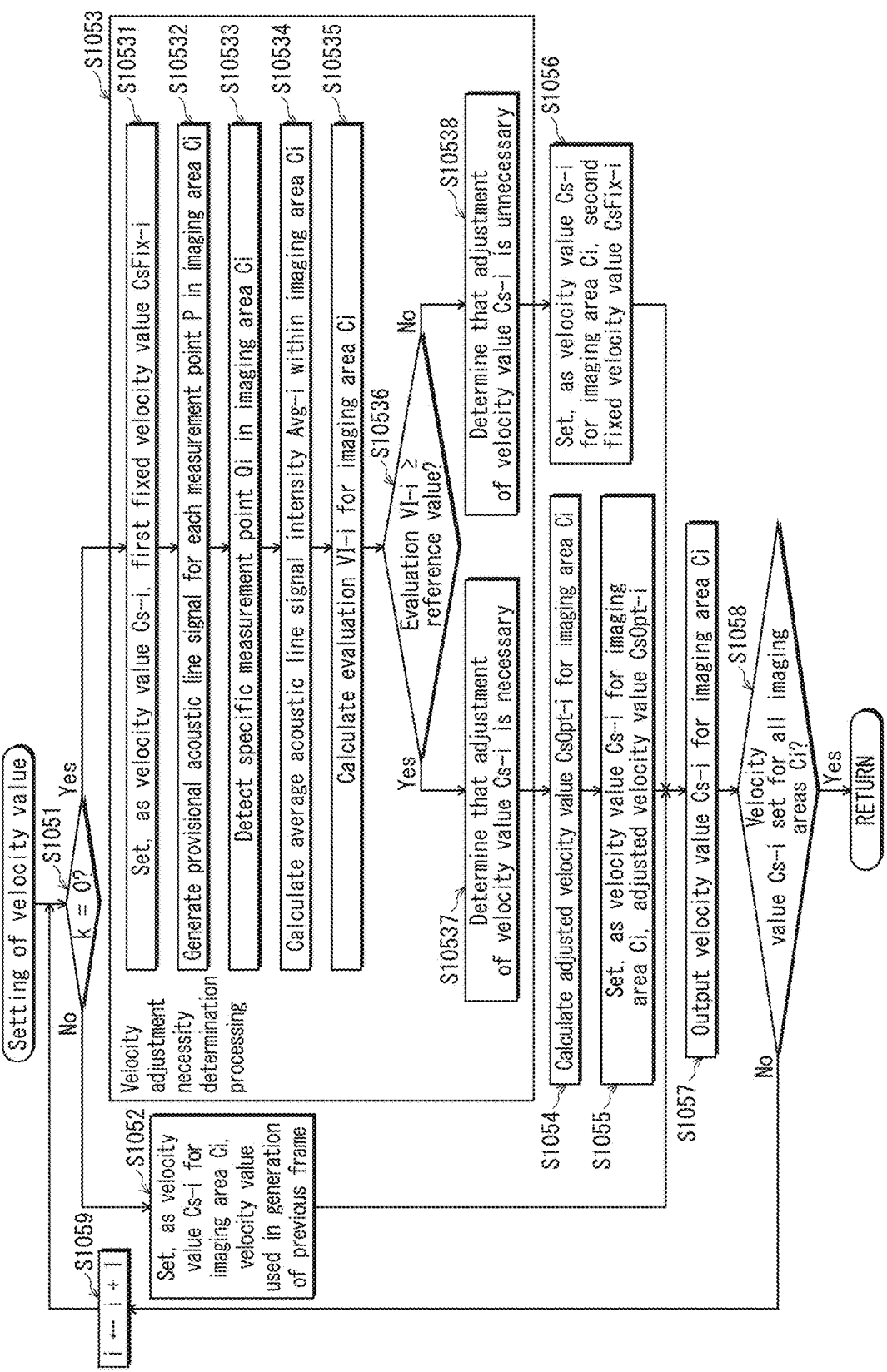
FIG. 14 is a flowchart illustrating velocity setting processing (Step S105) in the ultrasound diagnostic device 100.

FIG. 14 is a flowchart illustrating velocity setting processing (Step S105) for an imaging area Ci, in the ultrasound diagnostic device 100.

First, a determination is made of whether or not the processing is included in the initial generation of a frame ultrasound image following the commencement of ultrasound examination (Step S1051).

When the processing is not included in the initial generation of a frame ultrasound image (i.e., when the processing is for generating a second or any subsequent frame ultrasound image), the velocity value calculator 1045, based on an instruction from the control unit 108, sets the velocity value Cs−i that has been used in the generation of the previous frame ultrasound image and that is stored in the velocity value holder/outputter 10453, as the velocity value Cs−i of the imaging area Ci in the current frame (Step S1052). Subsequently, processing proceeds to Step S1057.

Meanwhile, when the processing is included in the initial generation of a frame ultrasound image, processing for determining the necessity of velocity value adjustment is performed (Step S1053).

In Step S1053, the fixed velocity value setter 10452, based on an instruction from the control unit 108, sets the fixed velocity value CsFix−i (the first fixed velocity) as the velocity value Cs−i for the imaging area Ci, and outputs the fixed velocity value CsFix−i to the velocity holder/outputter 10453. The velocity value calculator 1045 outputs, to the delay-and-sum processor 1043, the fixed velocity value CsFix−i stored in the velocity holder/outputter 10453 as the velocity value Cs−i for the imaging area Ci (Step S10531). Subsequently, the delay-and-sum processor 1043 generates a provisional acoustic line for each measurement point P in the imaging area Ci (Step S10532), and outputs the provisional acoustic line signals to the acoustic line signal holder 10441.

Subsequently, the specific measurement point detector 10443 detects the specific measurement point Qi in the imaging area Ci (Step S10533) by searching for a measurement point P with maximum acoustic line signal intensity Max−i. The specific measurement point detector 10443 searches for the specific measurement point Qi by comparing the acoustic line signal intensities of the respective measurement points P within a search area Di set in the imaging area Ci. Subsequently, the average calculator 10444 calculates an average Avg−i of acoustic line signal intensities of the respective measurement points included in an average calculation area Ei set in the imaging area Ci (Step S10534). Then, the evaluation calculator 10445, based on Equation (1) or Equation (2), calculates an evaluation Vl−i for the imaging area Ci, which is used in the determination of the necessity of adjusting the velocity value Cs−i for the imaging area Ci (Step S10535). Subsequently, the determination processor 10446 performs the determination of the necessity of adjusting the velocity value Cs−i for the imaging area Ci (Step S10536).

When the evaluation Vl−i is equal to or greater than the reference value, the determination processor 10446 determines that the velocity value Cs−i for the imaging area Ci needs to be adjusted. (Step S10537). Then, the adjusted velocity value calculator 10451 calculates an adjusted velocity value CsOpt−i for the imaging area Ci by using the acoustic line signal for the specific measurement point Qi in the imaging area Ci (Step S1054), and outputs the adjusted velocity value CsOpt−i to the velocity value holder/outputter 10453. Subsequently, the velocity value holder/outputter 10453 sets the velocity value Cs−i for the imaging area Ci based on the adjusted velocity value CsOpt−i (Step S1055). The adjusted velocity value calculation processing (Step S1054) is described in detail later in the present disclosure.

Meanwhile, when the evaluation Vl−i is smaller than the reference value, the determination processor 10446 determines that the velocity value Cs−i for the imaging area Ci does not need to be adjusted. (Step S10538). Then, the fixed velocity value setter 10452, based on an instruction from the control unit 108, outputs the fixed velocity value CsFix−i (the second fixed velocity) to the velocity value holder/outputter 10453. Subsequently, the velocity value holder/outputter 10453 sets the fixed velocity value CsFix−i as the velocity value Cs−i for the imaging area Ci (Step S1056).

Then, the velocity value calculator 1045 outputs, to the delay-and-sum processor 1043, the velocity value Cs−i for the imaging area Ci stored in the velocity value holder/outputter 10453 (Step S1057). Further, the velocity value calculator 1045 determines whether or not a velocity value Cs−i has been set with respect to all of the imaging areas Ci (Step S1058). When a velocity value Cs−i has not yet been set for one or more imaging areas Ci, the value i is incremented (Step S1059), and processing returns to Step S1051. Meanwhile, when velocity values Cs−i for all of the imaging areas Ci have been set, the velocity setting processing is terminated.

3. Adjusted Velocity Value Calculation Processing

Figure 15:
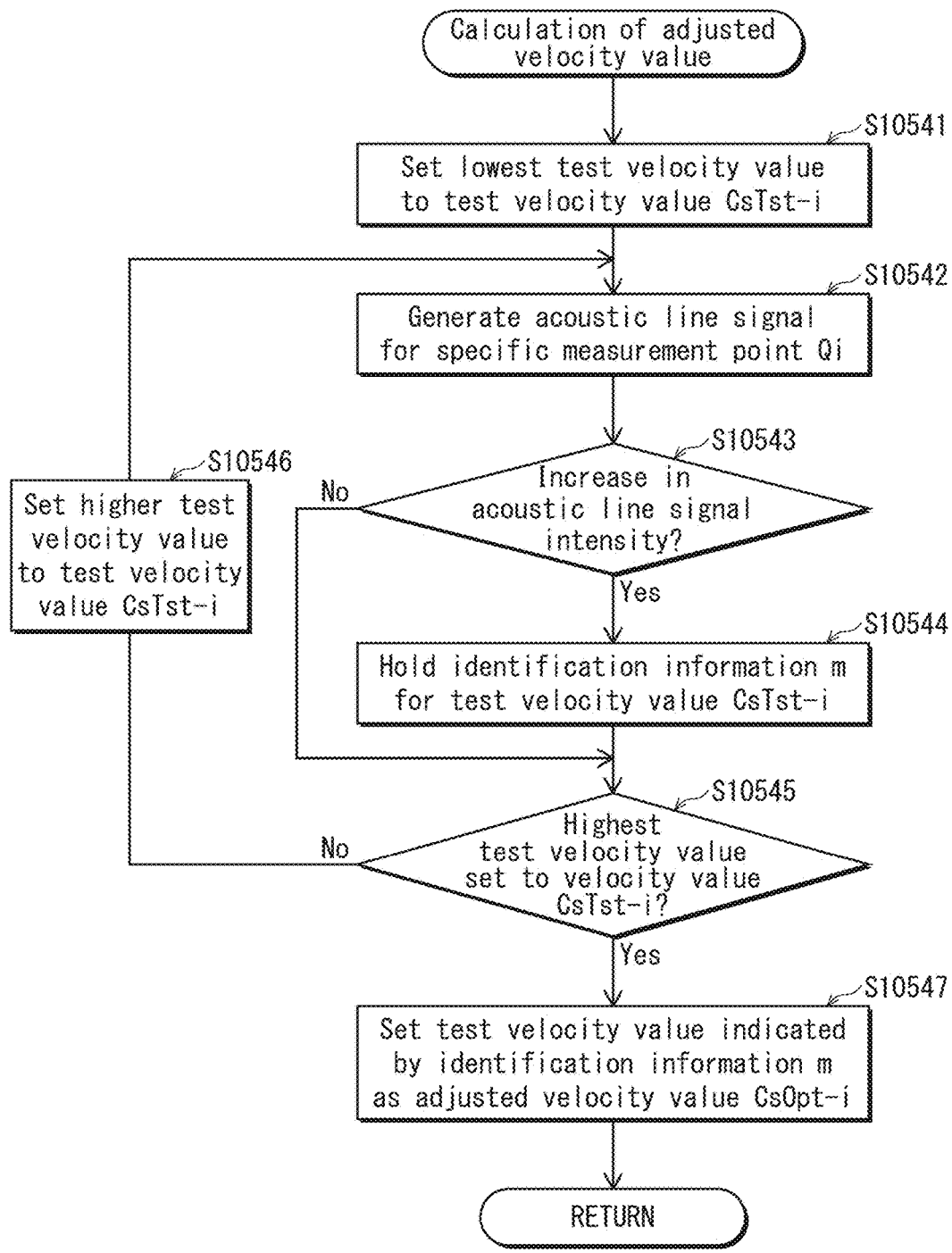
FIG. 15 is a flowchart illustrating adjusted velocity value calculation processing (Step S1054) in the ultrasound diagnostic device 100.

FIG. 15 is a flowchart illustrating the adjusted velocity value calculation processing (Step S1054) in the ultrasound diagnostic device 100.

In Step S10451, when acquiring from the determiner 1044 a determination result Jdg−i indicating that the velocity value Cs−i for the imaging area Ci needs to be adjusted, the test velocity value setter 104511 sets, for example, the minimum test velocity value CsTst−i within the range of 1400 m/s to 1590 m/s as the velocity value Cs−i for the imaging area Ci, and outputs this velocity value Cs−i to the delay-and-sum processor 1043.

Then, the delay-and-sum processor 1043 generates a provisional acoustic line signal for the specific measurement point Qi in the imaging area Ci by performing delay-and-sum processing by using the test velocity value CsTst−i (Step S10542).

Subsequently, the maximum acoustic line signal intensity detector 104513 determines whether or not the signal intensity of the provisional acoustic line signal so generated is greater than the signal intensity of an acoustic line signal stored in the specific measurement point acoustic line signal holder 104512 (Step S10543). Here, note that the maximum acoustic line signal intensity detector 104513 performs the same determination even when Step S10543 is executed for the first time and thus, the specific measurement point acoustic line signal holder 104512 does not hold an acoustic line signal.

When the signal intensity of the provisional acoustic line signal is equal to or greater than the signal intensity of the acoustic line signal stored in the specific measurement point acoustic line signal holder 104512, identification information m identifying the test velocity value CsTst–i having been used in the generation of the provisional acoustic line signal in Step S10542 is output to be stored in the adjusted velocity value determiner 104514 (Step S10544), and processing proceeds to Step S10545. Meanwhile, when the signal intensity of the provisional acoustic line signal is smaller than the signal intensity of the acoustic line signal stored in the specific measurement point acoustic line signal holder 104512, processing also proceeds to Step S10545, where a determination is performed of whether or not the current test velocity value CsTst–i is the maximum test velocity value CsTst–i within the range of 1400 m/s to 1590 m/s (Step S10545). When the current test velocity value CsTst–i is not the maximum test velocity value CsTst–i, the test velocity value CsTst–i is incremented to a greater value (Step S10546), and processing returns to Step S10542. Meanwhile, when the current test velocity value CsTst–i is the maximum test velocity value CsTst–i, the test velocity value CsTst–i indicated by the identification information m stored in the adjusted velocity value determiner 104514 is output as the adjusted velocity value CsOpt–i for the imaging area Ci (Step S10547). The adjusted velocity value CsOpt–i is output to the velocity value holder/outputter 10453.

<Evaluation Experiments>

1. Appropriateness of Adjusted Velocity Values Calculated Based on Specific Measurement Points In one experiment conducted in the process for arriving at the ultrasound diagnostic device 100, the present inventor performed an evaluation of the appropriateness of adjusted velocity values CsOpt–i, each calculated by specifying a test velocity value CsTst–i that yields maximum acoustic line intensity Max–i of a specific measurement point Qi. This experiment was conducted by excluding, from the processing by the ultrasound diagnostic device 100, the processing of determining the necessity of adjusting the velocity value for each image area Ci.

Figure 16:
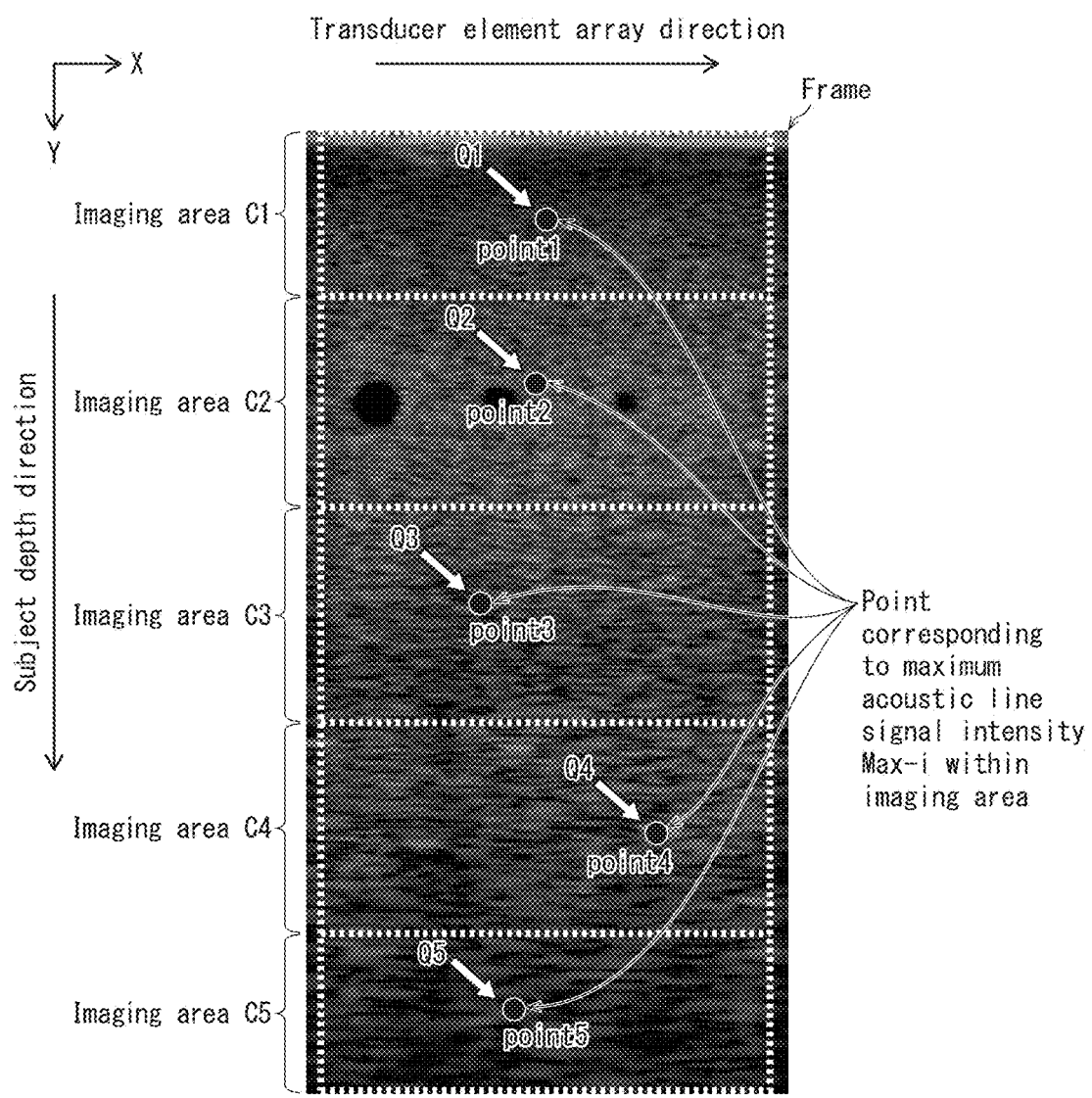
FIG. 16 shows an ultrasound image of an ultrasound phantom used for evaluating adjusted velocity values in the process for arriving at the ultrasound diagnostic device 100.

FIG. 16 shows an ultrasound image of an ultrasound phantom used for the evaluation of adjusted velocity values. The default velocity of the phantom was within the range of 1470±10 m/s. The frame of the ultrasound image shown in FIG. 16 is divided into five areas along the depth direction. Specifically, the frame is divided into imaging areas C1 through C5, each of which has the same width in the transducer element array direction as the transducer element array provided to the probe. Further, FIG. 16 shows specific measurement points Q1 through Q5 (points 1 through 5) respectively specified in the imaging areas C1 through C5. Each specific measurement point is a measurement point with maximum acoustic line signal intensity within the corresponding imaging area. FIG. 17 shows the results of the evaluation of adjusted velocity values. Specifically, FIG. 17 shows the results when, for each of the specific measurement point Q1 through Q5, different test velocity values CsTst–i were applied and the test velocity value CsTst–i yielding the maximum acoustic line signal intensity Max–i of the specific measurement point was set as the adjusted velocity value CsOpt–i for the imaging area including the specific measurement point. In this experiment, the adjusted velocity value CsOpt–i for imaging area C1, which is calculated based on the specific measurement point Q1, and the adjusted velocity value CsOpt–i for imaging area C5, which is calculated based on the specific measurement point Q5, each indicated an abnormal value that differed considerably from the default velocity of the phantom.

This experiment shows that when an adjusted velocity value CsOpt–i for an imaging area Ci is calculated by (i) selecting a specific measurement point Qi having the maximum acoustic line signal intensity within the imaging area Ci as a measurement point representing the imaging area Ci and (ii) setting a test velocity value CsTst–i yielding a maximum acoustic line signal intensity Max–i at the specific measurement point Qi as the adjusted velocity value CsOpt–i for the imaging area Ci, the adjusted velocity value CsOpt–i may be calculated to have an abnormal value differing considerably from the default velocity. According to an assumption made by the present inventor, this difference between the adjusted velocity value CsOpt–i and the default velocity is brought about by, for example, multiple reflection occurring near the transducer element array, decrease in reflected ultrasound signal intensity occurring at deep portions of the subject, a decrease in reliability of reflected ultrasound waves that are received occurring due to decrease in reflected ultrasound signal intensity at speckle portions corresponding to low density tissue.

3. Appropriateness of Velocity Adjustment based on Adjusted Velocity Values

In one experiment conducted in the process for arriving at the ultrasound diagnostic device 100, the present inventor observed the appropriateness of velocity value adjustment in the ultrasound diagnostic device 100 by causing the display unit 106 to display B-mode images generated by the ultrasound image generator 105 based on frame acoustic line signals.

Figure 18:
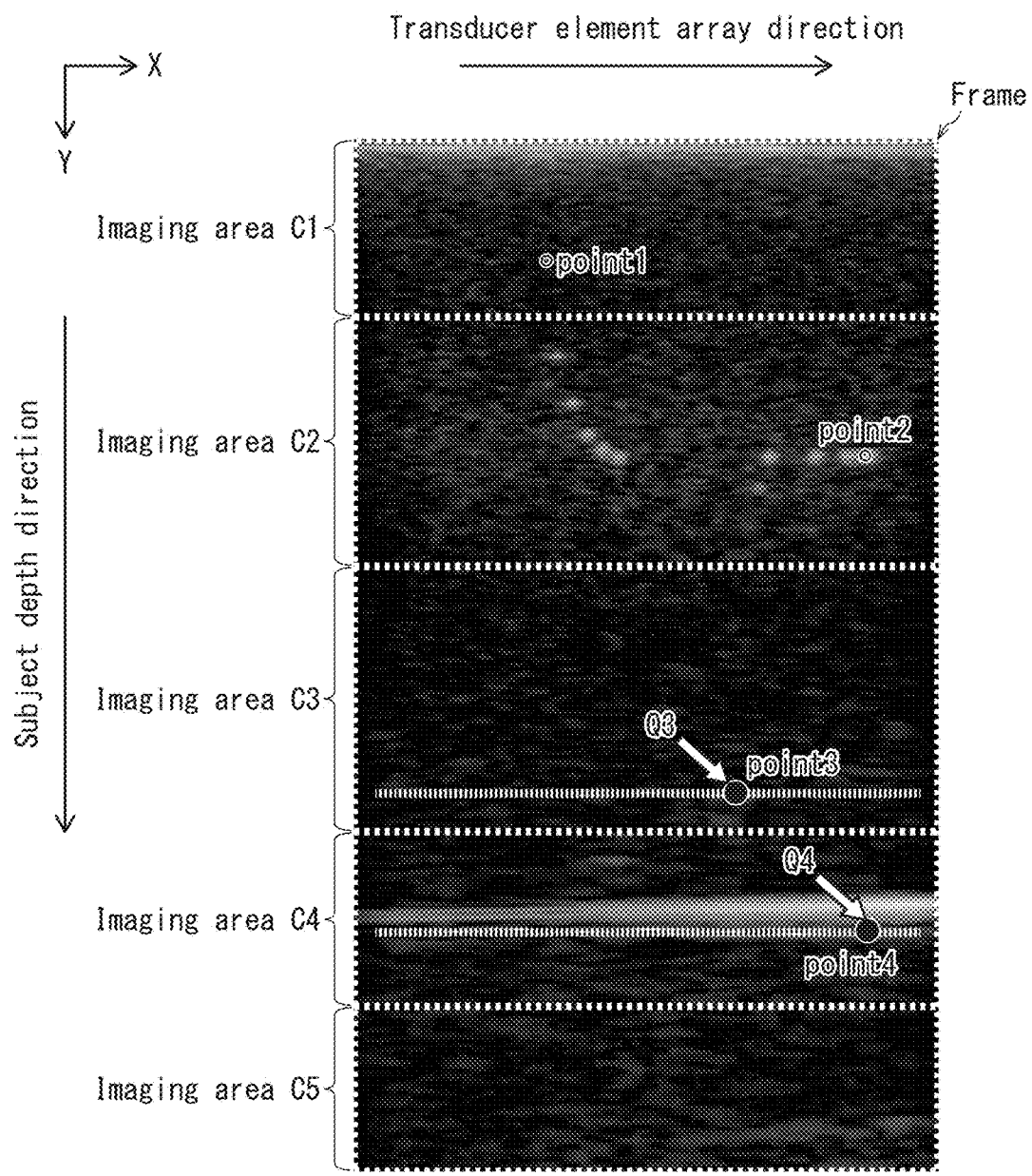
FIG. 18 shows an ultrasound image used in the evaluation of changes in acoustic line signal intensity brought about by application of test velocity values, conducted by using the ultrasound diagnostic device 100.

FIGS. 18 and 20 each show an ultrasound image used in the evaluation of changes in acoustic line signal intensity achieved by the ultrasound diagnostic device 100 by application of test velocity values. The frame of the ultrasound image shown in each of FIGS. 18 and 20 is divided into five areas along the depth direction. Specifically, the frame is divided into imaging areas C1 through C5, each of which has a same width in the transducer element array direction as the transducer element array provided to the probe. Further, each of FIGS. 18 and 20 shows specific measurement points Q1 through Q4 (points 1 through 4) respectively specified in the imaging areas C1 through C4. In the experiment, for each of specific measurement points Q3 and Q4, acoustic line signal intensities were calculated for measurement points located at the same depth as the specific measurement point, by using three different test velocity values CsTst–i. Each of FIGS. 19A and 19B shows waveforms of acoustic line signal intensities of measurement points located at the same depth as the specific measurement point, calculated by using the ultrasound diagnostic device 100 and based on the three different test velocity values CsTst–i. Specifically, FIG. 19A shows the results for the specific measurement point Q3 in FIG. 18, and FIG. 19B shows the results for the specific measurement point Q4 in FIG. 18.

As shown in FIG. 19A, the graphs corresponding to specific measurement point Q3 each increase sharply and reach a peak at the specific measurement point Q3. The peak in each graph has a height corresponding to approximately four times the change in acoustic line signal intensities observed at the other measurement points located at the same depth as the specific measurement point Q3. Meanwhile, the graphs corresponding to the three different test velocity values CsTst-i had different acoustic line signal intensities near the specific measurement point Q3.

Similarly, as shown in FIG. 19B, the graphs corresponding to specific measurement point Q4 each reach a peak at the specific measurement point Q4. However, the peak in each graph has a height substantially similar to the change in acoustic line signal intensities observed at the other measurement points located at the same depth as the specific measurement point Q4. Further, the graphs corresponding to the three different test velocity values CsTst-i overlapped one another near the specific measurement point Q4 and indicated similar acoustic line signal intensities near the specific measurement point Q4.

Further, FIG. 21 shows a change in acoustic line signal intensities of each of the specific measurement points Q1 and Q4 in FIG. 20, calculated by using the ultrasound diagnostic device 100 and based on different test velocity values CsTst-i.

As illustrated in FIG. 21, for the specific measurement point Q1, the acoustic line signal intensities calculated by using the twenty different text velocities CsTst-i formed a convex graph having a peak at the central portion thereof. Further, the maximum acoustic line signal intensity was yielded when using a test velocity value CsTst-i of approximately 1470 m/s. Meanwhile, for the specific measurement point Q4, the acoustic line signal intensities calculated by using the twenty different text velocities CsTst-i formed a planar graph, from which a particular test velocity value CsTst-i yielding a clear maximum acoustic line signal intensity could not be specified.

The above experiment results show that for each of specific measurement point Q3 (FIG. 18) and specific measurement point Q1 (FIG. 20), whose graphs of acoustic line signal intensity indicated sharp peaks, the use of different test velocity values brings about a change in acoustic line signal intensity at and around the specific measurement point. Accordingly, for imaging areas Ci including such measurement points, acoustic line signal intensity can be substantially maximized by setting a test velocity value CsTst-i yielding maximum acoustic line signal intensity at the specific measurement point as the adjusted velocity value CsOpt-i for the imaging area Ci, and generating acoustic line signals by performing delay-and-sum processing by using the adjusted velocity value CsOpt-i. In other words, for imaging areas including such specific measurement points, the processing of calculating an adjusted velocity value suiting the examination-target part proves to be efficient, due to an acoustic line signal with increased intensity being calculated for a measurement point included in the imaging area by receive signals based on ultrasound reflection from the measurement point being delay-and-summed appropriately.

On the other hand, the above experiment results show that for specific measurement point Q4 (FIGS. 18 and 20), whose graph of acoustic line signal intensity did not indicate a clear peak, the acoustic line signal intensity at the specific measurement point remains substantially the same, regardless of different test velocity values being used. Accordingly, for imaging areas Ci including such a specific measurement point, acoustic line signal intensity cannot be maximized by setting a test velocity value CsTst-i yielding maximum acoustic line signal intensity at the specific measurement point as the adjusted velocity value CsOpt-i for the imaging area Ci, and generating acoustic line signals by performing delay-and-sum processing by using the adjusted velocity value CsOpt-i. Further, the fact that the acoustic line signal intensity of the specific measurement point Q4 remains substantially the same means that the acoustic line signal intensity of the specific measurement point Q4 remains substantially the same for any test velocity values within the above range. Thus, it can be said that for imaging areas including such a specific measurement point, the processing of calculating an adjusted velocity value suiting the examination-target part is unnecessary.

3. Evaluation of Appropriateness of Function of Ultrasound Diagnostic Device 100 of Determining Necessity of Velocity Value Adjustment In order to confirm the appropriateness of the function of the ultrasound diagnostic device 100 of determining the necessity of velocity value adjustment, evaluation was performed by causing B-mode images generated by the ultrasound image generator 105 based on frame acoustic line signals to be displayed on the display unit 106.

FIGS. 22A, 22B, and 22C show the results of the evaluation of the function of the ultrasound diagnostic device 100 of determining the necessity of velocity value adjustment. Specifically, FIG. 22A shows evaluation results when the examination-target part was a tendon, FIG. 22B shows evaluation results when the examination-target part was a cyst, and FIG. 22C shows evaluation results when the examination-target part was white matter.

In the experiment for each examination-target part, the examination-target part was divided into five imaging areas C1 through C5, and a specific measurement point Qi (measurement point having maximum acoustic line signal intensity Max-i) was specified in each of the imaging areas Ci. Further, for each imaging area Ci, an evaluation Vl-i was calculated based on a ratio between the maximum acoustic line signal intensity Max-i and the average acoustic line signal intensity within the average calculation area Ei set in the imaging area Ci.

The evaluation of the function of determining the necessity of velocity value adjustment was performed through (i) for each imaging area Ci, setting the test velocity value CsTst-i yielding the maximum acoustic line signal intensity Max-i for the specific measurement point Qi as the adjusted velocity value CsOpt-i for the imaging area Ci, (ii) for each imaging area Ci, performing delay-and-sum processing with respect to the measurement points included in the imaging area Ci by using the adjusted velocity value CsOpt-i for the imaging area Ci and thereby generating acoustic line signals for the respective measurement points included in the imaging area Ci, (iii) generating an ultrasound image by using the acoustic line signals generated for the multiple imaging areas Ci, and (iv) checking whether or not an improvement in image quality was observed in the ultrasound image so generated. In FIGS. 22A through 22C, an imaging area Ci with the symbol ⊚ (double circle) is an imaging area Ci where an improvement in image quality was observed by applying an adjusted velocity value CsOpt-i, whereas an imaging area with the symbol ○ (circle) is an imaging area Ci where no improvement in image quality was observed by applying an adjusted velocity value CsOpt-i. Here, an imaging area Ci where an improvement in image quality was observed by applying an adjusted velocity value CsOpt-i is provided with the symbol ⊚, since application of an adjusted velocity value CsOpt-i provides such an imaging area Ci with higher image quality. Meanwhile, an imaging area Ci where no improvement in image quality was observed by applying an adjusted velocity value CsOpt-i is provided with the symbol ○, since image quality of such an imaging area Ci does not change with test velocity values CsTst-i within a predetermined range (for example, a range from 1400 m/s to 1590 m/s), and thus, since such an imaging area Ci has image quality of a certain level regardless of the velocity value used.

According to FIGS. 22A, 22B, and 22C, image quality of imaging areas Ci with evaluations Vl-i equal to or higher than 5.71 was improved by applying adjusted velocity values CsOpt-i. Accordingly, it is preferable that a determination that velocity value adjustment is necessary be made for imaging areas Ci with evaluations Vl-i equal to or higher than 5.71.

Meanwhile, according to FIGS. 22A, 22B, and 22C, image quality of imaging areas Ci with evaluations Vl-i equal to or lower than 5.43 did not change by applying adjusted velocity values CsOpt-i. Accordingly, it is preferable that a determination that velocity value adjustment is not necessary be made for imaging areas with evaluations Vl-i equal to or lower than 5.43.

Based on the above, a configuration is made such that a determination that velocity value adjustment is necessary is made for imaging areas Ci with evaluations VI-i equal to or higher than a threshold value 5.5, which is the median of the two values discussed above, and a determination that velocity value adjustment is unnecessary is made for imaging areas Ci with evaluations VI-i lower than the threshold value 5.5.

Accordingly, the risk is suppressed of an adjusted velocity value CsOpt-i having an abnormal value differing considerably from a default velocity being acquired by calculating an adjusted velocity value CsOpt-i for an imaging area Ci through (i) selecting a specific measurement point Qi having the maximum acoustic line signal intensity within the imaging area Ci as a measurement point representing the imaging area Ci and (ii) setting a test velocity value CsTst-i yielding a maximum acoustic line signal intensity Max-i at the specific measurement point Qi as the adjusted velocity value CsOpt-i for the imaging area Ci.

<Effects>

As discussed up to this point, the ultrasound diagnostic device 100 pertaining to the embodiment sets a plurality of imaging areas Ci by dividing a frame (an area for which an ultrasound image is rendered) indicated by a frame acoustic line signal into a plurality of areas, and in each imaging area Ci, selects a measurement point having maximum acoustic line signal intensity among the measurement points in the imaging area Ci as a measurement point representing the imaging area Ci (a specific measurement point Qi).

Further, the ultrasound diagnostic device 100 has a determiner that, for each imaging area Ci, performs a determination of the necessity of adjusting a velocity value Cs for the imaging area, based on the acoustic line signal intensity of the specific measurement point Qi and acoustic line signal intensities of at least some of the measurement points included in the imaging area Ci.

Further, the ultrasound diagnostic device 100 has an adjusted velocity value calculator that, when the determiner determines that velocity value adjustment is necessary for a given imaging area Ci, sets a test velocity value CsTst-i yielding a maximum acoustic line signal intensity Max-i of the specific measurement point Qi in the imaging area Ci as an adjusted velocity value CsOpt-i for the imaging area Ci.

Due to being configured in such a manner, the ultrasound diagnostic device 100 is capable of calculating an adjusted velocity value CsOpt-i for an imaging area Ci through simple computation of preemptively performing delay-and-sum processing with respect to only the specific measurement point Qi in the imaging area Ci, which is a measurement point representing the imaging area Ci.

Further, the ultrasound diagnostic device 100 performs the determination of the necessity of adjusting a velocity value Cs for an imaging area Ci, based on the acoustic line signal intensity of the specific measurement point Qi and acoustic line signal intensities of at least some of the measurement points included in the imaging area Ci. Due to this, the determination of the necessity of adjusting a velocity value Cs for the imaging area Ci requires only simple computation, and further, the risk is suppressed of an adjusted velocity value CsOpt-i having an abnormal value differing considerably from a default velocity being acquired.

As such, the ultrasound diagnostic device 100 is capable of carrying out the determination of the necessity of adjusting a velocity value Cs for an imaging area Ci in the process of generating an ultrasound image. Due to this, the ultrasound diagnostic device 100 eliminates the necessity of stopping ultrasound examination in order to perform velocity calibration (calibration for adjusting velocity to be suitable for the current examination-target part) each time the examination-target part is changed. Thus, the ultrasound diagnostic device 100 achieves high examination efficiency, as well as achieving simple device operation during examination.

<Modification 1>

As illustrated in FIG. 6, the ultrasound diagnostic device 100 pertaining to the embodiment divides a frame indicated by a frame acoustic line signal into a plurality of imaging areas Ci along the depth direction. However, the arrangement of imaging areas Ci in a frame may be changed as necessary, as long as each imaging area Ci is an area composed of measurement points for which the same velocity value Cs is to be applied in delay-and-sum processing.

FIG. 23 is a schematic illustrating imaging areas Ci pertaining to modification 1. In modification 1, a frame is divided along both the depth direction and the transducer element array direction, to acquire imaging areas Ci forming a matrix (imaging areas C11-C13, C21-C23, C31-C33, C41-43, and C51-C53). Setting such imaging areas Ci in a frame achieves, for each of the imaging areas Ci, generating acoustic line signals for the measurement points included in the imaging area Ci by using an adjusted velocity value that suits the tissue of the examination-target part in both the depth direction and the transducer element array direction. Accordingly, even when tissue composition differs in the direction parallel to the subject surface, image quality improvement can be achieved.

Alternatively, a modification may be made of setting a plurality of imaging areas Ci by dividing a frame indicated by a frame acoustic line signal into a plurality of areas Ci along a direction that is parallel to the subject surface and that is perpendicular to the depth direction.

<Modification 2>

The ultrasound diagnostic device 100 pertaining to the embodiment performs the determination of whether the processing is included in the initial generation of a frame ultrasound image following the commencement of ultrasound examination. Further, when the processing is not included in the initial generation of a frame ultrasound image (i.e., when the processing is for generating a second or any subsequent frame ultrasound image), the ultrasound diagnostic device 100 sets, for an imaging area Ci, a velocity value Cs−i that has been used in the generation of a previous frame ultrasound image as the velocity value Cs−i of the imaging area Ci in the current frame, and performs delay-and-sum processing with respect to the imaging area Ci by using the velocity value so set. Meanwhile, when the processing is included in the initial generation of a frame ultrasound image, the ultrasound diagnostic device 100 performs processing for determining the necessity of velocity value adjustment. However, the ultrasound diagnostic device 100 may also perform the determination of the necessity of velocity value adjustment for example, when the user of the ultrasound diagnostic device 100 performs input via an input receiver (e.g., a control panel of the ultrasound diagnostic device 100 or a button provided to the probe 101).

When making such a modification, even for example when the user changes the examination-target part, the ultrasound diagnostic device 100 is capable of generating acoustic line signals by performing delay-and-sum processing by using adjusted velocity values suitable for the tissue of the new examination-target part without stopping ultrasound examination. Due to this, even when performing ultrasound examination by moving the probe along the subject surface over an examination-target area whose tissue composition differs in the direction parallel to the subject surface, image quality improvement can be achieved. Further, when making such a modification, the ultrasound diagnostic device 100 eliminates the necessity of stopping ultrasound examination in order to perform velocity calibration (calibration for adjusting velocity to be suitable for the current examination-target part) each time the examination-target part is changed. Thus, the ultrasound diagnostic device 100 achieves high examination efficiency, as well as achieving simple device operation during examination.

<Modification 3>

The transmission beam former 103 and the receive beam former 104 need not have the respective structures described in the embodiment. That is, the structure of each of the transmission beam former 103 and the receive beam former 104 may be changed as necessary. For example, in the embodiment, the transmitter 1031 sets a transmission aperture Tx that is composed of some of the transducer elements 101a provided to the probe 101, and repetitively performs ultrasound transmission while shifting the transmission aperture Tx in the transducer element array direction each time so that all of the transducer elements 101a of the probe 101 transmit ultrasound.

Alternatively, the transmitter 1031 may cause all of the transducer elements 101a provided to the probe 101 to transmit ultrasound all at once. This modification eliminates the necessity of repeating ultrasound transmission, and achieves reception of reflected ultrasound from the entirety of the ultrasound irradiation area Ax through one ultrasound transmission event.

In addition, in the embodiment, the calculation-target area Bx is a linear area that has a width corresponding to one transducer element, that passes through a center position of a corresponding receive aperture Rx, and that is perpendicular to the transducer element array direction.

However, the calculation target area Bx is not limited to such an area, and may be any area within the ultrasound irradiation area Ax. For example, the calculation target area Bx may be a rectangular area that has a belt-like shape, that has a width corresponding to two or more transducer elements, that passes through a center position of a corresponding receive aperture Rx, and that has a central axis perpendicular to the transducer element array direction. Alternatively, the calculation target area Bx may be an area having an hourglass-shape similar to the ultrasound irradiation area Ax. Further, the calculation target areas Bx for different transmission events may overlap one another in the transducer element array direction. Making this modification and synthesizing acoustic line signals for overlapping areas of the calculation target areas Bx based on the synthetic aperture method achieves an ultrasound image with high S/N ratio.

<Other Modifications>

Up to this point, the technology pertaining to the present disclosure has been described based on specific embodiments and modifications thereof. However, the embodiments and modifications described above are non-limiting examples of application of the technology pertaining to the present disclosure, and thus, the technology pertaining to the present disclosure shall be construed to encompass the following exemplar modifications.

For example, the technology pertaining to the present disclosure may be implemented by using a computer system including a memory storing a computer program and a microprocessor operating based on the computer program. For example, the computer system may store a computer program of a diagnosis method of an ultrasound diagnostic device pertaining to the technology of the present disclosure, and the computer system may operate in accordance with the computer program or may provide instructions in accordance with the computer program to various components connected thereto.

Further, the technology pertaining to the present disclosure may be implemented by implementing a part of or the entirety of an ultrasound diagnostic device described above, or a part of or an entirety of an beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the technology pertaining to the present disclosure may be implemented by implementing some or all constituent elements included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each constituent element may be separately implemented by using one chip, or some or all constituent elements may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the technology pertaining to the present disclosure encompasses a form of implementation where an LSI stores a beam forming method pertaining to the present disclosure as a program, the LSI is inserted into a computer, and the computer executes the program (i.e., the beam forming method pertaining to the present disclosure).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiments may be implemented by a processor such as a CPU executing a program. Further, the technology pertaining to the present disclosure may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

Each of the ultrasound diagnostic devices pertaining to the embodiments includes the data storage, which is a recording device. However, the recording device need not be included in the ultrasound diagnostic devices, and may be implemented by using a semiconductor memory, a hard disk drive, an optical disk drive, a magnetic storage device, or the like connected to the ultrasound diagnostic devices from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the technology pertaining to the present disclosure. Further, some of the steps of processing described above may be executed simultaneously (in parallel).

Further, in the embodiments, description is provided that the ultrasound diagnostic devices may have a probe and a display attached thereto. However, the ultrasound diagnostic devices may include a probe and a display therein.

Further, in the embodiments, the probe includes a plurality of piezoelectric transducer elements forming a line in one direction. However, the probe may have a different structure. For example, the probe may include a plurality of piezoelectric transducer elements disposed two-dimensionally. Alternatively, the probe may be a swingable probe including a plurality of swingable transducer elements (i.e., transducer elements that can be caused to swing by mechanical means) forming a line in one direction, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of the transmission beam former/receive beam former. For example, the probe may be capable of generating a transmission electric signal based on a control signal that the transmission beam former/receive beam former outputs to cause generation of a transmission electric signal, and of converting the transmission electronic signal into ultrasound. In addition, the probe may be capable of converting reflected ultrasound into a receive electric signal, and of generating a receive signal based on the receive electric signal.

Further, at least some of the functions of the ultrasound diagnostic devices pertaining to the embodiments and the modifications may be combined with functions of other ones of the ultrasound diagnostic devices pertaining to the embodiments and the modifications. Further, the values used above are non-limiting examples used for the sole sake of providing specific description of the technology pertaining to the present disclosure, and may be replaced with other values.

Further, the technology pertaining to the present disclosure should be construed as encompassing various modifications that a skilled artisan would arrive at based on the embodiments describe above.

<<Conclusion>>

One aspect of the present disclosure is an ultrasound diagnostic device to which an ultrasound probe having a plurality of transducer elements is connectable, including: ultrasound signal processing circuitry operating as: a delay-and-sum processor that, for each of a plurality of measurement points respectively corresponding to different positions within a subject, generates an acoustic line signal for the measurement point by summing receive signals for the measurement point, the receive signals respectively corresponding to some or all of the transducer elements and each being generated based on ultrasound reflection that one transducer element receives in response to ultrasound transmission by some or all of the transducer elements towards the subject, wherein for each of the some or all of the transducer elements, the receive signal corresponding to the measurement point is specified taking into account a relative delay in arrival of the ultrasound reflection at the transducer element, the delay being calculated based on a relative distance between the measurement point and the transducer element and a velocity value being an estimated value of ultrasound velocity of a partial area including the measurement point, the partial area corresponding to an area within the subject and being a group of ones of the measurement points for which the same velocity value is applied in the calculation of the delay; a determiner that determines whether or not the velocity value for the partial area is to be adjusted, based on an intensity of an acoustic line signal for a specific measurement point included in the partial area, and intensities of acoustic line signals for at least some of the measurement points included in the partial area, the specific measurement point specified from among the measurement points included in the partial area based on acoustic line signals for at least some of the measurement points included in the partial area; and a velocity value calculator that, when the determiner determines that the velocity value for the partial area is to be adjusted, calculates an adjusted velocity value for the partial area by using the acoustic line signal for the specific measurement point.

This structure achieves calculating an adjusted velocity value to be used in delay-and-sum processing through simple calculation. In addition, this structure achieves performing the determination of the necessity of velocity value adjustment through simple calculation, and reducing the risk of an adjusted velocity value differing considerably from a default velocity value being acquired.

In the ultrasound diagnostic device, the delay-and-sum processor may generate acoustic line signals, one for each of the measurement points included in the partial area, by using a predetermined first fixed velocity value, the determiner may specify the specific measurement point based on the acoustic line signals generated by using the predetermined first fixed velocity value, and may determine whether or not the predetermined first fixed velocity value is to be adjusted, based on an intensity of one of the acoustic line signals generated by using the predetermined first fixed velocity value that corresponds to the specific measurement point and intensities of ones of the acoustic line signals generated by using the predetermined first fixed velocity value that correspond to at least some of the measurement points included in the partial area, and when the determiner determines that the predetermined first fixed velocity value is to be adjusted, the velocity value calculator may calculate an adjusted velocity value for the partial area, and the delay-and-sum processor generates acoustic line signals, one for each of the measurement points in the partial area, by using the adjusted velocity value, and when the determiner determines that the predetermined first fixed velocity value is not to be adjusted, the delay-and-sum processor may generate acoustic line signals, one for each of the measurement points in the partial area, by using a predetermined second fixed velocity value.

This structure achieves performing the determination of the necessity of velocity value adjustment as a part of processing for generating an ultrasound image, thereby achieving high examination efficiency and simple device operation during examination.

In the ultrasound diagnostic device, the acoustic line signal for the specific measurement point may have greater intensity than an acoustic line signal for any of the rest of the measurement points included in the partial area.

Further, in the ultrasound diagnostic device, the determiner may determine whether or not the velocity value for the partial area is to be adjusted, based on a ratio between the intensity of the acoustic line signal for the specific measurement point and an average intensity of the acoustic line signals for the at least some of the measurement points included in the partial area.

These structures achieve calculating an adjusted velocity value to be used in delay-and-sum processing and determining the necessity of velocity value adjustment through simple calculation.

In the ultrasound diagnostic device, the at least some of the measurement points, whose acoustic line signals are used to calculate the average intensity, may be ones of the measurement points included in the partial area that correspond to a same depth in the subject as the specific measurement point.

Further, in the ultrasound diagnostic device, the at least some of the measurement points, whose acoustic line signals are used to calculate the average intensity, may be ones of the measurement points included in the partial area that are located within a predetermined distance from the specific measurement point.

Further, in the ultrasound diagnostic device, the at least some of the measurement points, whose acoustic line signals are used to calculate the average intensity, may be ones of the measurement points included in the partial area that are located on and within a predetermined distance from a virtual line indicating a same depth in the subject as the specific measurement point.

These structures achieve performing the determination of the necessity of velocity value adjustment with high accuracy and through simple calculation.

In the ultrasound diagnostic device, the determiner may determine that the velocity value for the partial area is to be adjusted at least when the ratio is greater than or equal to a predetermined threshold.

Further, in the ultrasound diagnostic device, the determiner may determine that the velocity value for the partial area is to be adjusted when the ratio is greater than or equal to the predetermined threshold, and determine that the velocity value for the partial area is not to be adjusted when the ratio is smaller than the predetermined threshold.

These structures achieve reducing the risk of an adjusted velocity value differing considerably from a default velocity value being acquired.

In the ultrasound diagnostic device, a plurality of partial areas may be set, and for each of the plurality of partial areas, the determiner may perform the determination of whether or not the velocity value for the partial area is to be adjusted. Here, the plurality of partial areas may be arranged to form a matrix.

This structure achieves performing the determination of the necessity of velocity value adjustment with high accuracy. In addition, this structure achieve generating an acoustic line signal for a measurement point by performing delay-and-sum processing by using an adjusted velocity value suitable for the examination-target part including the measurement point in both the depth direction and the transducer element array direction. Accordingly, this structure achieves image quality improvement even when tissue composition differs in the direction parallel to the subject surface.

In the ultrasound diagnostic device, the predetermined second fixed velocity value may be at least 1525 m/s and at most 1545 m/s.

This structure achieves calculating an appropriate adjusted velocity value to be used in delay-and-sum processing through a simple calculation.

In the ultrasound diagnostic device, the plurality of partial areas may each correspond to a different depth range within the subject.

Further, in the ultrasound diagnostic device, the predetermined second fixed velocity value for a given partial area may be a velocity value applied to a first adjacent partial area or a velocity value applied to a second adjacent partial area, the first and second adjacent partial areas being two partial areas that are adjacent to the given partial area and that are located at opposing sides of the given partial area with the given partial area therebetween.

Further, in the ultrasound diagnostic device, the predetermined second fixed velocity value for a given partial area may be an average of a velocity value applied to a first adjacent partial area and a velocity value applied to a second adjacent partial area, the first and second adjacent partial areas being two partial areas that are adjacent to the given partial area and that are located at opposing sides of the given partial area with the given partial area therebetween.

These structures achieve calculating an adjusted velocity value to be used in delay-and-sum processing with high accuracy and through simple calculation.

In the ultrasound diagnostic device, the velocity value calculator may calculate the adjusted velocity value for the partial area by causing the delay-and-sum processor to perform the generation of the acoustic line signal for the specific measurement point multiple times, each time using one of a plurality of velocity values within a predetermined range, and by setting one of the plurality of velocity values providing the acoustic line signal for the specific measurement point with greatest intensity as the adjusted velocity value.

This structure achieves calculating an adjusted velocity value suitable for the tissue of the examination-target part through a simple calculation.

Another aspect of the present disclosure is a method for controlling an ultrasound diagnostic device to which an ultrasound probe having a plurality of transducer elements is connectable, the method including: generating an acoustic line signal for each of a plurality of measurement points forming a partial area corresponding to an area within a subject, by summing receive signals for the measurement point, the receive signals respectively corresponding to some or all of the transducer elements and each being generated based on ultrasound reflection that one transducer element receives in response to ultrasound transmission by some or all of the transducer elements towards the subject, wherein for each of the some or all of the transducer elements, the receive signal corresponding to the measurement point is specified taking into account a relative delay in arrival of the ultrasound reflection at the transducer element, the delay being calculated based on a relative distance between the measurement point and the transducer element and a predetermined first fixed velocity value being an estimated value of ultrasound velocity of the partial area; determining whether or not the first fixed velocity value is to be adjusted, based on an intensity of an acoustic line signal for a specific measurement point included in the partial area, and intensities of acoustic line signals for at least some of the measurement points included in the partial area, the specific measurement point specified from among the measurement points included in the partial area based on acoustic line signals for at least some of the measurement points included in the partial area; when the determining determines that the first fixed velocity value is to be adjusted, calculating an adjusted velocity value for the partial area by using the acoustic line signal for the specific measurement point, and generating acoustic line signals, one for each of the measurement points included in the partial area, by using the adjusted velocity value; and when the determining determines that the first fixed velocity value is not to be adjusted, generating acoustic line signals, one for each of the measurement points included in the partial area, by using a predetermined second fixed velocity value.

This structure achieves calculating an adjusted velocity value to be used in delay-and-sum processing through a simple calculation. In addition, this structure achieves performing the determination of the necessity of velocity value adjustment through a simple calculation, and reducing the risk of an adjusted velocity value differing considerably from a default velocity value being acquired. Further, this structure achieves performing the determination of the necessity of velocity value adjustment as a part of processing for generating an ultrasound image, thereby achieving high examination efficiency and simple device operation during examination.

In the method, the acoustic line signal for the specific measurement point may have greater intensity than an acoustic line signal for any of the rest of the measurement points included in the partial area.

This structure achieves calculating an adjusted velocity value to be used in delay-and-sum processing through a simple calculation.

In the method, the determining may determine whether or not the first fixed velocity value is to be adjusted, based on a ratio between the intensity of the acoustic line signal for the specific measurement point and an average intensity of the acoustic line signals for the at least some of the measurement points included in the partial area, and may determine that the first fixed velocity value is to be adjusted at least when the ratio is greater than or equal to a predetermined threshold.

This structure achieves performing the determination of the necessity of velocity value adjustment through a simple calculation, and reducing the risk of an adjusted velocity value differing considerably from a default velocity value being acquired.

<<Supplement>>

Each of the embodiments described above should be construed as being a preferable and specific example of implementation of the technology pertaining to the present disclosure. As such, any value, any shape, any material, any constituent element, any position of any constituent element, any connection of any constituent element, any step, and any order in which any step is performed shall be construed as being a non-limiting example. Further, among the constituent elements described in the embodiments, any constituent element not recited in the independent claims, which represent the broadest concept of the present disclosure, shall be construed as a constituent element not necessarily essential but included in a preferable form of implementation of the technology pertaining to the present disclosure.

Further, in order to facilitate understanding, constituent elements described in the embodiments may be illustrated in drawings at a scale differing from their actual sizes. Further, the technology pertaining to the present disclosure shall not be construed as being limited to the embodiments, and instead, shall be construed as encompassing any modification that does not depart from the spirit and the scope of the present disclosure.

Further, the embodiments and modifications do not provide description of circuit parts and lead wires disposed on substrates in ultrasound diagnostic devices. This is since various forms of electric wiring and electric circuitry are implementable based on knowledge possessed by a skilled artisan in the present field of technology, and are not directly essential in describing the technology pertaining to the present disclosure. Further, all drawings referred to in the above are schematic drawings and may not be accurate in a strict sense.

Although the technology pertaining to the present disclosure has been fully described by way of examples with reference to the accompanying drawings, it is to be noted that various changes and modifications will be apparent to those skilled in the art. Therefore, unless such changes and modifications depart from the scope of the present disclosure, they should be construed as being included therein.

What is claimed is:

1. An ultrasound diagnostic device to which an ultrasound probe having a plurality of transducer elements is connectable, comprising:
ultrasound signal processing circuitry operating as:
a delay-and-sum processor that, for each of a plurality of measurement points respectively corresponding to different positions within a subject, generates an acoustic line signal for the measurement point by summing receive signals for the measurement point, the receive signals respectively corresponding to some or all of the transducer elements and each being generated based on ultrasound reflection that one transducer element receives in response to ultrasound transmission by some or all of the transducer elements towards the subject, wherein for each of the some or all of the transducer elements, the receive signal corresponding to the measurement point is specified taking into account a relative delay in arrival of the ultrasound reflection at the transducer element, the delay being calculated based on a relative distance between the measurement point and the transducer element and a velocity value being an estimated value of ultrasound velocity of a partial area including the measurement point, the partial area corresponding to an area within the subject and being a group of ones of the measurement points for which the same velocity value is applied in the calculation of the delay;
a determiner that determines whether or not the velocity value for the partial area is to be adjusted, based on an intensity of an acoustic line signal for a specific measurement point included in the partial area, and intensities of acoustic line signals for at least some of the measurement points included in the partial area, the specific measurement point specified from among the measurement points included in the partial area based on acoustic line signals for at least some of the measurement points included in the partial area; and
a velocity value calculator that, when the determiner determines that the velocity value for the partial area is to be adjusted, calculates an adjusted velocity value for the partial area by using the acoustic line signal for the specific measurement point.

2. The ultrasound diagnostic device of claim 1, wherein
the delay-and-sum processor generates acoustic line signals, one for each of the measurement points included in the partial area, by using a predetermined first fixed velocity value,
the determiner specifies the specific measurement point based on the acoustic line signals generated by using the predetermined first fixed velocity value, and determines whether or not the predetermined first fixed velocity value is to be adjusted, based on an intensity of one of the acoustic line signals generated by using the predetermined first fixed velocity value that corresponds to the specific measurement point and intensities of ones of the acoustic line signals generated by using the predetermined first fixed velocity value that correspond to at least some of the measurement points included in the partial area, and
when the determiner determines that the predetermined first fixed velocity value is to be adjusted, the velocity value calculator calculates an adjusted velocity value for the partial area, and the delay-and-sum processor generates acoustic line signals, one for each of the measurement points in the partial area, by using the adjusted velocity value, and when the determiner determines that the predetermined first fixed velocity value is not to be adjusted, the delay-and-sum processor generates acoustic line signals, one for each of the measurement points in the partial area, by using a predetermined second fixed velocity value.

3. The ultrasound diagnostic device of claim 1, wherein the acoustic line signal for the specific measurement point has greater intensity than an acoustic line signal for any of the rest of the measurement points included in the partial area.

4. The ultrasound diagnostic device of claim 1, wherein the determiner determines whether or not the velocity value for the partial area is to be adjusted, based on a ratio between the intensity of the acoustic line signal for the specific measurement point and an average intensity of the acoustic line signals for the at least some of the measurement points included in the partial area.

5. The ultrasound diagnostic device of claim 4, wherein the at least some of the measurement points, whose acoustic line signals are used to calculate the average intensity, are ones of the measurement points included in the partial area that correspond to a same depth in the subject as the specific measurement point.

6. The ultrasound diagnostic device of claim 4, wherein the at least some of the measurement points, whose acoustic line signals are used to calculate the average intensity, are ones of the measurement points included in the partial area that are located within a predetermined distance from the specific measurement point.

7. The ultrasound diagnostic device of claim 4, wherein the at least some of the measurement points, whose acoustic line signals are used to calculate the average intensity, are ones of the measurement points included in the partial area that are located on and within a predetermined distance from a virtual line indicating a same depth in the subject as the specific measurement point.

8. The ultrasound diagnostic device of claim 4, wherein the determiner determines that the velocity value for the partial area is to be adjusted at least when the ratio is greater than or equal to a predetermined threshold.

9. The ultrasound diagnostic device of claim 4, wherein the determiner determines that the velocity value for the partial area is to be adjusted when the ratio is greater than or equal to the predetermined threshold, and determines that the velocity value for the partial area is not to be adjusted when the ratio is smaller than the predetermined threshold.

10. The ultrasound diagnostic device of claim 1, wherein a plurality of partial areas are set, and
for each of the plurality of partial areas, the determiner performs the determination of whether or not the velocity value for the partial area is to be adjusted.

11. The ultrasound diagnostic device of claim 2, wherein the predetermined second fixed velocity value is at least 1525 m/s and at most 1545 m/s.

12. The ultrasound diagnostic device of claim 10, wherein the plurality of partial areas each correspond to a different depth range within the subject.

13. The ultrasound diagnostic device of claim 12, wherein the predetermined second fixed velocity value for a given partial area is a velocity value applied to a first adjacent partial area or a velocity value applied to a second adjacent partial area, the first and second adjacent partial areas being two partial areas that are adjacent to the given partial area and that are located at opposing sides of the given partial area with the given partial area therebetween.

14. The ultrasound diagnostic device of claim 12, wherein the predetermined second fixed velocity value for a given partial area is an average of a velocity value applied to a first adjacent partial area and a velocity value applied to a second adjacent partial area, the first and second adjacent partial areas being two partial areas that are adjacent to the given partial area and that are located at opposing sides of the given partial area with the given partial area therebetween.

15. The ultrasound diagnostic device of claim 1, wherein the velocity value calculator calculates the adjusted velocity value for the partial area by causing the delay-and-sum processor to perform the generation of the acoustic line signal for the specific measurement point multiple times, each time using one of a plurality of velocity values within a predetermined range, and by setting one of the plurality of velocity values providing the acoustic line signal for the specific measurement point with greatest intensity as the adjusted velocity value.

16. A method for controlling an ultrasound diagnostic device to which an ultrasound probe having a plurality of transducer elements is connectable, the method comprising:
generating an acoustic line signal for each of a plurality of measurement points forming a partial area corresponding to an area within a subject, by summing receive signals for the measurement point, the receive signals respectively corresponding to some or all of the transducer elements and each being generated based on ultrasound reflection that one transducer element receives in response to ultrasound transmission by some or all of the transducer elements towards the subject, wherein for each of the some or all of the transducer elements, the receive signal corresponding to the measurement point is specified taking into account a relative delay in arrival of the ultrasound reflection at the transducer element, the delay being calculated based on a relative distance between the measurement point and the transducer element and a predetermined first fixed velocity value being an estimated value of ultrasound velocity of the partial area;

determining whether or not the first fixed velocity value is to be adjusted, based on an intensity of an acoustic line signal for a specific measurement point included in the partial area, and intensities of acoustic line signals for at least some of the measurement points included in the partial area, the specific measurement point specified from among the measurement points included in the partial area based on acoustic line signals for at least some of the measurement points included in the partial area;

when the determining determines that the first fixed velocity value is to be adjusted, calculating an adjusted velocity value for the partial area by using the acoustic line signal for the specific measurement point, and generating acoustic line signals, one for each of the measurement points included in the partial area, by using the adjusted velocity value; and when the determining determines that the first fixed velocity value is not to be adjusted, generating acoustic line signals, one for each of the measurement points included in the partial area, by using a predetermined second fixed velocity value.

17. The method of claim 16, wherein
the acoustic line signal for the specific measurement point has greater intensity than an acoustic line signal for any of the rest of the measurement points included in the partial area.

18. The method of claim 16, wherein
the determining
determines whether or not the first fixed velocity value is to be adjusted, based on a ratio between the intensity of the acoustic line signal for the specific measurement point and an average intensity of the acoustic line signals for the at least some of the measurement points included in the partial area, and
determines that the first fixed velocity value is to be adjusted at least when the ratio is greater than or equal to a predetermined threshold.

\* \* \* \* \*